(12) United States Patent
Li et al.

(10) Patent No.: US 7,912,545 B2
(45) Date of Patent: *Mar. 22, 2011

(54) METHOD AND APPARATUS FOR MORPHOLOGY-BASED ARRHYTHMIA CLASSIFICATION USING CARDIAC AND OTHER PHYSIOLOGICAL SIGNALS

(75) Inventors: Dan Li, Shoreview, MN (US); Shelley M. Cazares, Washington, DC (US); Jaeho Kim, Redmond, WA (US); Kent Lee, Shoreview, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/536,828

(22) Filed: Aug. 6, 2009

(65) Prior Publication Data

US 2009/0292332 A1   Nov. 26, 2009

Related U.S. Application Data

(63) Continuation of application No. 11/316,332, filed on Dec. 22, 2005, now Pat. No. 7,582,061.

(51) Int. Cl.
*A61N 1/362* (2006.01)
*A61B 5/04* (2006.01)

(52) U.S. Cl. .................... 607/14; 600/508; 600/515

(58) Field of Classification Search .................. 600/508, 600/515; 607/14
See application file for complete search history.

(56) References Cited

U.S. PATENT DOCUMENTS

| | | | |
|---|---|---|---|
| 4,531,527 A | 7/1985 | Reinhold, Jr. et al. | |
| 4,583,553 A | 4/1986 | Shah et al. | |
| 4,947,857 A | 8/1990 | Albert et al. | |
| 5,000,189 A | 3/1991 | Throne et al. | |
| 5,215,098 A | 6/1993 | Steinhaus et al. | |
| 5,217,021 A | 6/1993 | Steinhaus et al. | |
| 5,240,009 A | 8/1993 | Williams | |
| 5,255,186 A | 10/1993 | Steinhaus et al. | |
| 5,266,554 A | 11/1993 | Suchy et al. | |
| 5,271,411 A | 12/1993 | Ripley et al. | |

(Continued)

FOREIGN PATENT DOCUMENTS

EP   0469817 A2   2/1992

(Continued)

OTHER PUBLICATIONS

"U.S. Appl. No. 11/316,332, Amendment and Response filed Jul. 6, 2009 to Notice of Allowance mailed Apr. 6, 2009", 15 pgs.

(Continued)

*Primary Examiner* — Carl H. Layno
*Assistant Examiner* — Jon-Eric C. Morales
(74) *Attorney, Agent, or Firm* — Schwegman, Lundberg & Woessner, P.A.

(57) ABSTRACT

A tachyarrhythmia detection and classification system classifies tachyarrhythmias based on an analysis of morphological features of a cardiac signal enhanced by using one or more physiological parameters indicative of hemodynamic stability and/or activity level. The tachyarrhythmia detection and classification system computes a measure of similarity between an arrhythmic waveform of the cardiac signal, a template waveform for that cardiac signal, such as a correlation coefficient representative of the correlation between morphological features of the arrhythmic waveform and morphological features of the template waveform. A detected tachyarrhythmia episode is classified by comparing the measure of similarity to a threshold that is dynamically adjusted using the one or more physiological parameters.

20 Claims, 14 Drawing Sheets

U.S. PATENT DOCUMENTS

| | | | |
|---|---|---|---|
| 5,273,049 A * | 12/1993 | Steinhaus et al. | 600/508 |
| 5,280,792 A | 1/1994 | Leong et al. | |
| 5,311,874 A | 5/1994 | Baumann et al. | |
| 5,366,487 A | 11/1994 | Adams et al. | |
| 5,400,795 A | 3/1995 | Murphy et al. | |
| 5,447,519 A | 9/1995 | Peterson | |
| 5,513,644 A | 5/1996 | McClure et al. | |
| 5,542,430 A | 8/1996 | Farrugia et al. | |
| 5,645,070 A | 7/1997 | Turcott | |
| 5,685,315 A | 11/1997 | McClure et al. | |
| 5,712,801 A | 1/1998 | Turcott | |
| 5,718,242 A | 2/1998 | McClure et al. | |
| 5,779,645 A | 7/1998 | Olson et al. | |
| 5,797,399 A | 8/1998 | Morris et al. | |
| 5,882,352 A | 3/1999 | Duncan et al. | |
| 6,192,273 B1 | 2/2001 | Igel et al. | |
| 6,266,554 B1 | 7/2001 | Hsu et al. | |
| 6,275,732 B1 | 8/2001 | Hsu et al. | |
| 6,526,313 B2 | 2/2003 | Sweeney et al. | |
| 6,684,100 B1 | 1/2004 | Sweeney et al. | |
| 6,728,572 B2 | 4/2004 | Hsu et al. | |
| 6,760,615 B2 | 7/2004 | Ferek-Petric | |
| 6,766,190 B2 | 7/2004 | Ferek-Petric | |
| 6,873,870 B2 | 3/2005 | Ferek-Petric | |
| 6,978,177 B1 | 12/2005 | Chen et al. | |
| 7,203,535 B1 | 4/2007 | Hsu et al. | |
| 7,212,849 B2 | 5/2007 | Zhang et al. | |
| 7,430,446 B2 | 9/2008 | Li | |
| 7,500,955 B2 | 3/2009 | Sweeney | |
| 7,582,061 B2 | 9/2009 | Li et al. | |
| 2002/0032469 A1 | 3/2002 | Marcovecchio | |
| 2002/0183639 A1 | 12/2002 | Sweeney et al. | |
| 2002/0188215 A1 | 12/2002 | Ferek-Petric | |
| 2002/0198461 A1 | 12/2002 | Hsu et al. | |
| 2003/0100923 A1 | 5/2003 | Bjorling et al. | |
| 2003/0120316 A1 | 6/2003 | Spinelli et al. | |
| 2003/0181818 A1 | 9/2003 | Kim et al. | |
| 2004/0015090 A1 | 1/2004 | Sweeney et al. | |
| 2004/0093035 A1 | 5/2004 | Schwartz et al. | |
| 2004/0127806 A1 | 7/2004 | Sweeney | |
| 2004/0260348 A1 | 12/2004 | Bakken et al. | |
| 2005/0256544 A1 | 11/2005 | Thompson | |
| 2006/0095083 A1 * | 5/2006 | Zhang et al. | 607/14 |
| 2006/0155201 A1 | 7/2006 | Schwartz et al. | |
| 2006/0281998 A1 | 12/2006 | Li | |
| 2007/0142737 A1 | 6/2007 | Cazares et al. | |
| 2007/0149890 A1 | 6/2007 | Li et al. | |
| 2007/0203419 A1 | 8/2007 | Sweeney et al. | |

FOREIGN PATENT DOCUMENTS

| | | |
|---|---|---|
| EP | 0506230 A1 | 9/1992 |
| EP | 554208 A2 | 8/1993 |
| EP | 0848965 A2 | 6/1998 |
| WO | WO-97/39681 A1 | 10/1997 |

OTHER PUBLICATIONS

"U.S. Appl. No. 11/316,332, Notice of Allowance mailed Apr. 6, 2009", 12 pgs.

"U.S. Appl. No. 11/316,332, Response to Rule 312 Communication mailed Jul. 20, 2009", 2 pgs.

Hegbom, F., et al., "RV Function in Stable and Unstable VT: is There a Need for Hemodynamic Monitoring in Future Defibrillators?", *Pacing and Clinical Electrophysiology*, 24(2), (Feb. 2001), 172-182.

Steinbach, K. K, et al., "Hemodynamics during ventricular tachyarrhythmias", *American Heart Journal*, 127(4, Part 2), (Apr. 1994), 1102-1106.

* cited by examiner

METHOD AND APPARATUS FOR MORPHOLOGY-BASED ARRHYTHMIA CLASSIFICATION USING CARDIAC AND OTHER PHYSIOLOGICAL SIGNALS

CROSS-REFERENCE TO RELATED APPLICATIONS

This application is a continuation of U.S. application Ser. No. 11/316,332, filed Dec. 22, 2005, now U.S. Pat. No. 7,582,061, which is hereby incorporated by reference in its entirety.

This application is related to, commonly assigned U.S. patent application Ser. No. 11/038,996, entitled "METHODS AND APPARATUSES FOR CARDIAC ARRHYTHMIA CLASSIFICATION USING MORPHOLOGY STABILITY," filed on Jan. 20, 2005, now issued as U.S. Pat. No. 7,430,446, which is hereby incorporated by reference in its entirety.

TECHNICAL FIELD

This document relates generally to cardiac rhythm management (CRM) systems and particularly, but not by way of limitation, to such a system providing for morphology-based tachyarrhythmia classification enhanced by using one or more physiologic signals such as hemodynamic and activity signals.

BACKGROUND

The heart is the center of a person's circulatory system. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These mechanical pumping functions are accomplished by contractions of the heart. In a normal heart, the sinoatrial (SA) node, the heart's natural pacemaker, generates electrical impulses, called action potentials, that propagate through an electrical conduction system to various regions of the heart to cause the muscular tissues of these regions to depolarize and contract. The electrical conduction system includes, in the order by which the electrical impulses travel in a normal heart, internodal pathways between the SA node and the atrioventricular (AV) node, the AV node, the His bundle, and the Purkinje system including the right bundle branch (RBB, which conducts the electrical impulses to the RV) and the left bundle branch (LBB, which conducts the electrical impulses to the LV). More generally, the electrical impulses travel through an AV conduction pathway to cause the atria, and then the ventricles, to contract.

Tachyarrhythmia occurs when the heart contracts at a rate higher than a normal heart rate. Tachyarrhythmia generally includes ventricular tachyarrhythmia (VT) and supraventricular tachyarrhythmia (SVT). VT occurs, for example, when a pathological conduction loop formed in the ventricles through which electrical impulses travel circularly within the ventricles, or when a pathologically formed electrical focus generates electrical impulses from the ventricles. SVT includes physiological sinus tachyarrhythmia and pathologic SVTs. The physiological sinus tachyarrhythmia occurs when the SA node generates the electrical impulses at a particularly high rate. A pathologic SVT occurs, for example, when a pathologic conduction loop forms in an atrium. Fibrillation occurs when the heart contracts at a tachyarrhythmia rate with an irregular rhythm. Ventricular fibrillation (VF), as a ventricular arrhythmia with an irregular conduction, is a life threatening condition requiring immediate medical treatment such as ventricular defibrillation. Atrial fibrillation (AF), as a SVT with an irregular rhythm, though not directly life threatening, also needs medical treatment such as atrial defibrillation to restore a normal cardiac function and to prevent the deterioration of the heart.

Implantable cardioverter/defibrillators (ICDs) are used to treat tachyarrhythmias, including fibrillation. To deliver an effective cardioversion/defibrillation therapy, the cardioversion/defibrillation energy is to be delivered to the chambers of the heart where the tachyarrhythmia or fibrillation originates. Morphology-based classification is a known approach to classifying a detected tachyarrhythmia episode. In one example, a detected tachyarrhythmia episode is classified by its origin by analyzing a correlation between morphological features of a cardiac signal sensed during the detected tachyarrhythmia episode and morphological features of a template signal sensed during a known type rhythm. However, morphological changes of a cardiac signal during a tachyarrhythmia episode may differ from patient to patient, as well as from time to time. Additionally, variations in the morphological features may also attribute to changes in other physiological factors. Therefore, there is a need to adjust the correlation analysis for various factors affecting the accuracy of morphology-based classification of tachyarrhythmias.

SUMMARY

A tachyarrhythmia detection and classification system classifies tachyarrhythmias based on an analysis of morphological features of a cardiac signal enhanced by using one or more physiological parameters indicative of hemodynamic stability and/or activity level. The tachyarrhythmia detection and classification system computes a measure of similarity between an arrhythmic waveform of the cardiac signal, a template waveform for that cardiac signal, such as a correlation coefficient representative of the correlation between morphological features of the arrhythmic waveform and morphological features of the template waveform. A detected tachyarrhythmia episode is classified by comparing the measure of similarity to a threshold that is dynamically adjusted using the one or more physiological parameters.

In one embodiment, a tachyarrhythmia detection and classification system includes a cardiac sensing circuit, a tachyarrhythmia detector, one or more physiological sensors, a physiological parameter generator, and a morphology-based tachyarrhythmia classification module. The cardiac sensing circuit senses at least one cardiac signal. The tachyarrhythmia detector detects a tachyarrhythmia episode from the cardiac signal. The one or more physiological sensors sense one or more physiological signals. The physiological parameter generator derives one or more physiological parameters from the one or more physiological signals. The morphology-based tachyarrhythmia classification module includes a feature extractor, a similarity analyzer, a classifier, and a threshold generator. The feature extractor extracts arrhythmic morphological features of an arrhythmic heart beat of the detected tachyarrhythmia episode from the at least one cardiac signal. The similarity analyzer computes a measure of similarity between the arrhythmic morphological features and template morphological features of a template heart beat of a known type cardiac rhythm. The classifier classifies the arrhythmic heart beat using the measure of similarity and a dynamically adjustable beat classification threshold. The threshold generator adjusts the beat classification threshold using the one or more physiological parameters.

In one embodiment, a method for detecting and classifying tachyarrhythmias is provided. At least one cardiac signal is sensed. A tachyarrhythmia episode is detected from the cardiac signal. Arrhythmic morphological features of an arrhythmic heart beat of the detected tachyarrhythmia episode are extracted from the cardiac signal. A measure of similarity between the arrhythmic morphological features and template morphological features of a template heart beat of a known type cardiac rhythm is computed for each arrhythmic heart beat of a plurality of arrhythmic heart beats. The detected tachyarrhythmia episode is classified using the values of the measure of similarity computed for the plurality of arrhythmic heart beats and a dynamically adjustable beat classification threshold. The beat classification threshold is dynamically adjusted using one or more physiological parameters derived from one or more sensed physiological signals.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings illustrate generally, by way of example, but not by way of limitation, various embodiments discussed in the present document.

DETAILED DESCRIPTION

Figure 1:
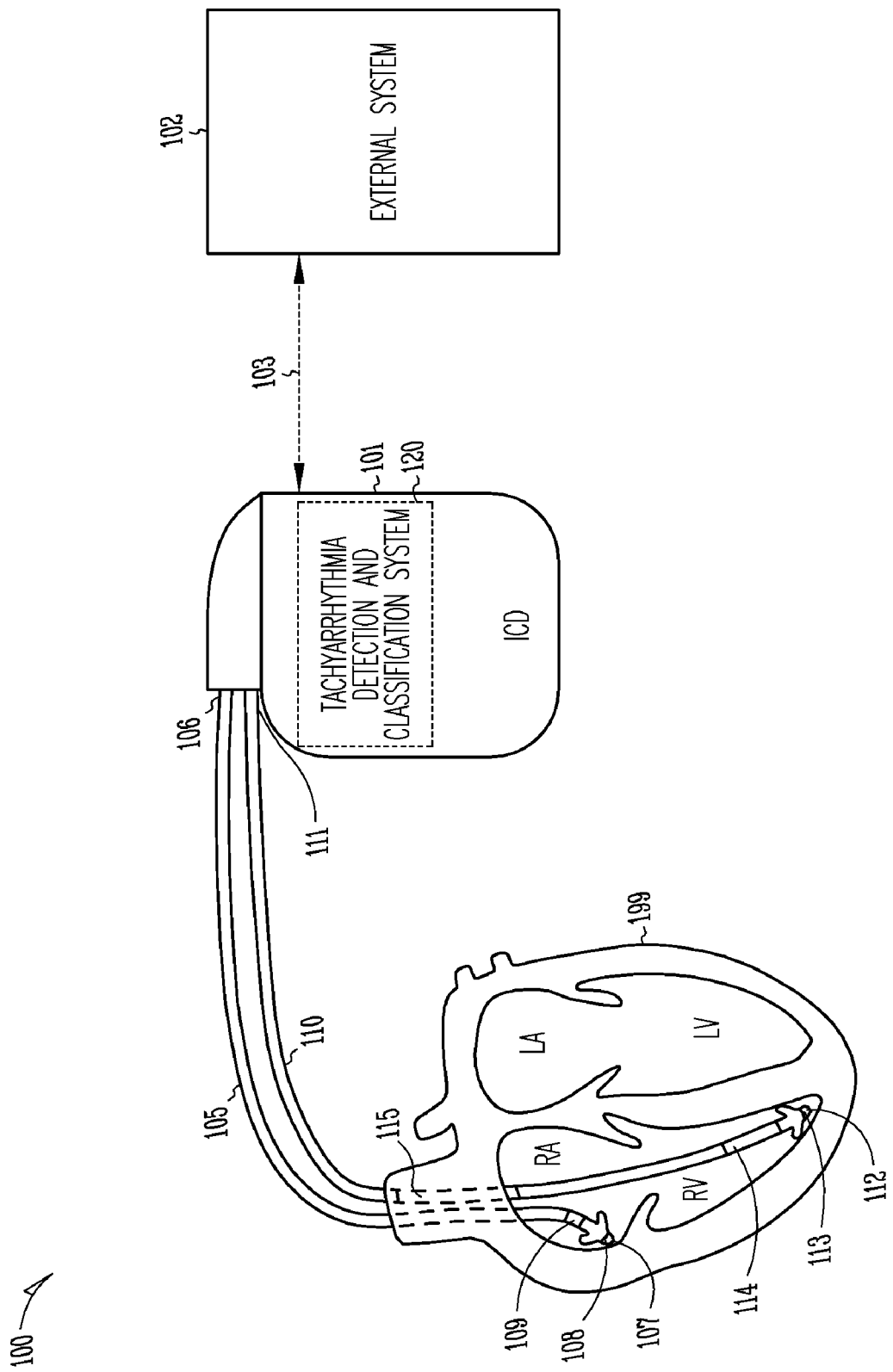
FIG. 1 is an illustration of one embodiment of a CRM system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this documents and those documents so incorporated by reference, the usage in the incorporated reference(s) should be considered supplementary to that of this document; for irreconcilable inconsistencies, the usage in this document controls.

It should be noted that references to "an", "one", or "various" embodiments in this document are not necessarily to the same embodiment, and such references contemplate more than one embodiment.

In this document, an "arrhythmic heart beat" includes a heart beat sensed during a detected tachyarrhythmia episode. An "arrhythmic waveform" includes a waveform (such as a segment of an electrogram) associated with an arrhythmic heart beat. "Arrhythmic morphological features" include morphological features of an arrhythmic waveform. A "template heart beat" represents a heart beat associated with a known cardiac rhythm and used as a "template" for a morphological analysis using morphological features associated with the known cardiac rhythm. The template heart beat may be produced from a plurality of hearts beats sensed during the known cardiac rhythm, such as by averaging. A "template waveform" includes a waveform associated with the template heart beat. "Template morphological features" include morphological features of the template waveform.

This document discusses, among other things, a CRM system that senses one or more cardiac signals and one or more other physiological signals. Examples of the one or more other physiological signals include hemodynamic signal indicative of a patient's hemodynamic performance and activity signal indicative of the patient's gross physical activity level. The CRM system includes a tachyarrhythmia detection and classification system that detects tachyarrhythmia episodes from the one or more cardiac signals and classifies each detected tachyarrhythmia episode by analyzing similarity between arrhythmic waveforms of the tachyarrhythmia episode and template waveforms. A measure of similarity is computed to indicate the degree of similarity between each of a plurality of arrhythmic heart beat and a template heart beat. The measure of similarity is compared to a beat classification threshold, and the tachyarrhythmia episode is classified based on the number of the arrhythmic heart beats associated with a measure of similarity that exceeds the beat classification threshold. The threshold is dynamically adjustable using at least a hemodynamic signal or an activity signal. Such dynamic threshold adjustment allows the morphology-based tachyarrhythmia classification to be adaptive to variations in conditions of the patient as well as variations in conditions among different patients' conditions.

In one embodiment, the measure of similarity is a correlation coefficient. The tachyarrhythmia detection and classification system classifies each detected tachyarrhythmia episode by computing correlation coefficients for a predetermined number of arrhythmic heart beats. The correlation coefficients are each between arrhythmic morphological features of an arrhythmic waveform and corresponding template morphological features of a template waveform. Each of the correlation coefficients is compared to a beat classification threshold, and the tachyarrhythmia episode is classified based on the number of the arrhythmic heart beats associated with a correlation coefficient that exceeds the beat classification threshold. The threshold is dynamically adjustable using at least the hemodynamic signal or the activity signal.

While the tachyarrhythmia detection and classification system is specifically discussed as part of an ICD in this document as an example, the present subject matter applies to tachyarrhythmia classification using an implantable or non-implantable system analyzing real-time sensed signals or recorded previously sensed signals.

FIG. 1 is an illustration of one embodiment of a CRM system 100 and portions of the environment in which CRM system 100 operates. CRM system 100 includes an ICD 101 that is electrically coupled to a heart 199 through leads 105 and 110. An external system 102 communicates with ICD 101 via a telemetry link 103.

ICD 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is a pacing lead that includes a proximal end 106 connected to ICD 101 and a distal end 107 disposed in the right atrium (RA) of heart 199. A pacing-sensing electrode 108 is located at distal end 107. Another pacing-sensing electrode 109 is located near distal end 107. Electrodes 108 and 109 are electronically connected to ICD 101 via separate conductors in lead 105 to allow sensing of the atrial electrogram and/or delivery of atrial pacing pulses. Lead 110 is a defibrillation lead that includes a proximal end 111 connected to ICD 101 and a distal end 112 disposed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to ICD 101 via separate conductors in lead 110. Electrode 113 allows sensing of the ventricular electrogram and/or delivery of ventricular pacing pulses. Electrodes 114 and 115 allow delivery of ventricular cardioversion/defibrillation pulses.

ICD 101 includes a tachyarrhythmia detection and classification system 120 that performs morphology-based tachyarrhythmia classification enhanced by using hemodynamic and/or activity information. In one embodiment, system 100 delivers a ventricular defibrillation pulse when a detected tachyarrhythmia episode is classified as a VT. The hemodynamic and/or activity information is used to reduce unnecessary deliveries of the ventricular defibrillation pulse that cause pain to the patient and shortens the longevity of ICD 101, as well as to ensure delivery of the ventricular defibrillation pulse when treatment is necessitated by hemodynamic instability.

External system 102 allows for programming of ICD 101 and receives signals acquired by ICD 101. In one embodiment, external system 102 includes a programmer. In another embodiment, external system 102 is a patient management system including an external device in proximity of ICD 101, a remote device in a relatively distant location, and a telecommunication network linking the external device and the remote device. The patient management system allows access to ICD 101 from a remote location, such as for monitoring patient status and adjusting therapies. In one embodiment, telemetry link 103 is an inductive telemetry link. In an alternative embodiment, telemetry link 103 is a far-field radio-frequency telemetry link. Telemetry link 103 provides for data transmission from ICD 101 to external system 102. This may include, for example, transmitting real-time physiological data acquired by ICD 101, extracting physiological data acquired by and stored in ICD 101, extracting therapy history data stored in ICD 101, and extracting data indicating an operational status of ICD 101 (e.g., battery status and lead impedance). Telemetry link 103 also provides for data transmission from external system 102 to ICD 101. This may include, for example, programming ICD 101 to acquire physiological data, programming ICD 101 to perform at least one self-diagnostic test (such as for a device operational status), programming ICD 101 to run a signal analysis algorithm (such as an algorithm implementing a tachyarrhythmia classification method discussed in this document), and programming ICD 101 to deliver pacing and/or cardioversion/defibrillation therapies.

Tachyarrhythmia detection and classification system 120 may be implemented using a combination of hardware and software. In various embodiments, each element of tachyarrhythmia detection and classification system 120, including its specific embodiments, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof. For example, a "comparator" includes, among other things, an electronic circuit comparator constructed to perform the only function of a comparison between two signals or a portion of a general-purpose circuit driven by a code instructing that portion of the general-purpose circuit to perform the comparison between the two signals.

Figure 2:
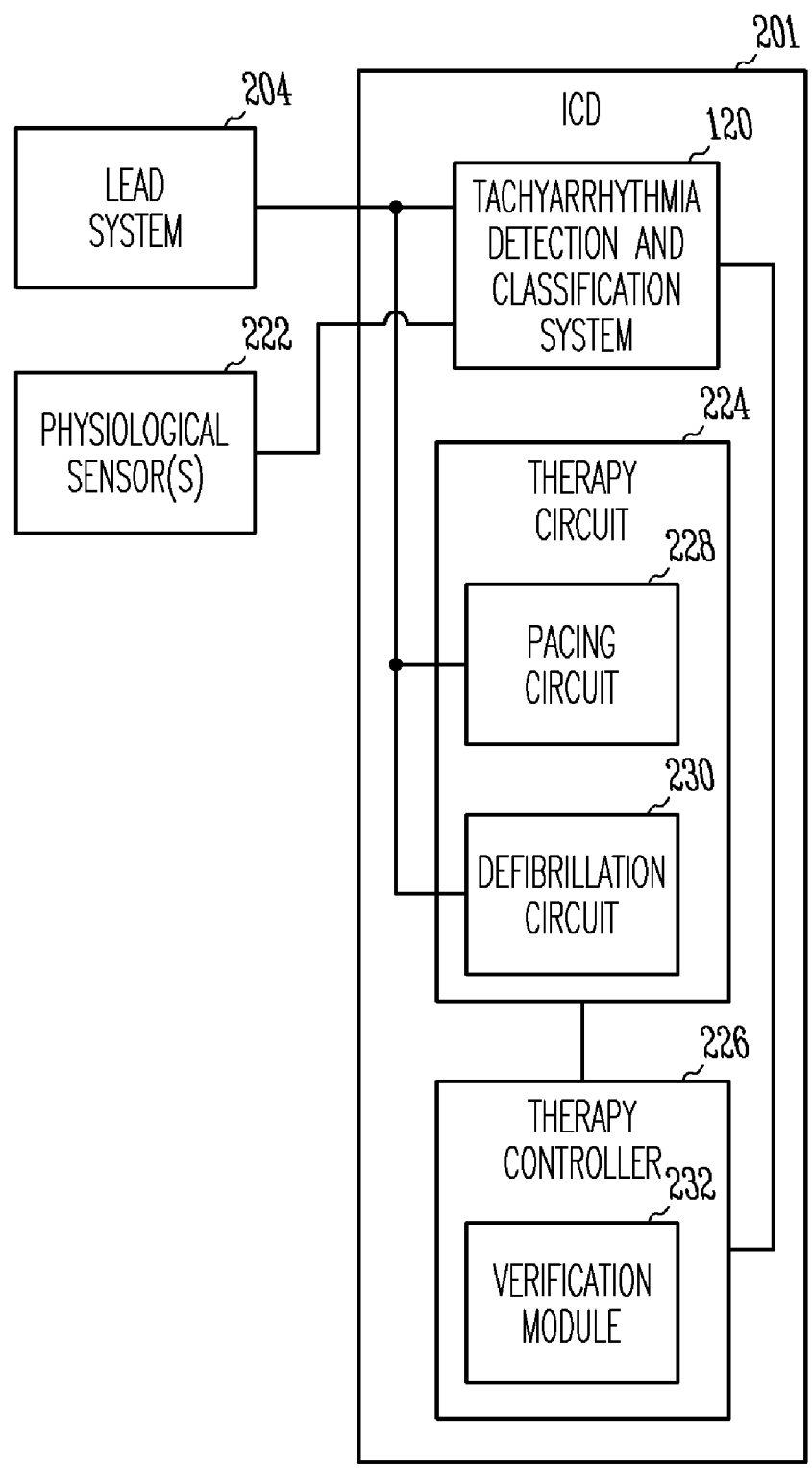
FIG. 2 is a block diagram illustrating a specific embodiment of portions of the CRM system including an ICD coupled to a lead system and one or more physiological sensors.

FIG. 2 is a block diagram illustrating a specific embodiment of portions of CRM system 100, including an ICD 201 coupled to a lead system 204 and one or more physiological sensors 222. Lead system 204 includes one or more leads such as leads 105 and 110. ICD 201 is a specific embodiment of ICD 101 and includes tachyarrhythmia detection and classification system 120, which detects and classifies tachyarrhythmia episode using one or more cardiac signals sensed using lead system 204 and one or more other physiological signals sensed using physiological sensor(s) 222. ICD 201 also includes a therapy circuit 224 and a therapy controller 226. Therapy circuit 224 includes a pacing circuit 228 to deliver pacing pulses to heart 199 through lead system 204 and a defibrillation circuit 230 to deliver cardioversion/defibrillation pulses to heart 199 through lead system 204. Therapy controller 226 controls the delivery of the pacing and/or cardioversion/defibrillation pulses using the classification of the tachyarrhythmia episode. In one embodiment, therapy controller 226 selects one of an anti-tachycardia pacing (ATP) and a cardioversion/defibrillation therapy based on the classification of the tachyarrhythmia episode. Therapy controller 226 includes a verification module 232 to verify effectiveness of a therapy following the delivery of that therapy. If the therapy is found ineffective, it is to be repeated, or a more aggressive type of therapy follows. For example, if the ATP therapy is selected and delivered but fails to terminate a detected tachyarrhythmia episode, the cardioversion/defibrillation therapy is delivered and the delivery is repeated, when necessary, until the detected tachyarrhythmia episode is terminated.

Figure 3:
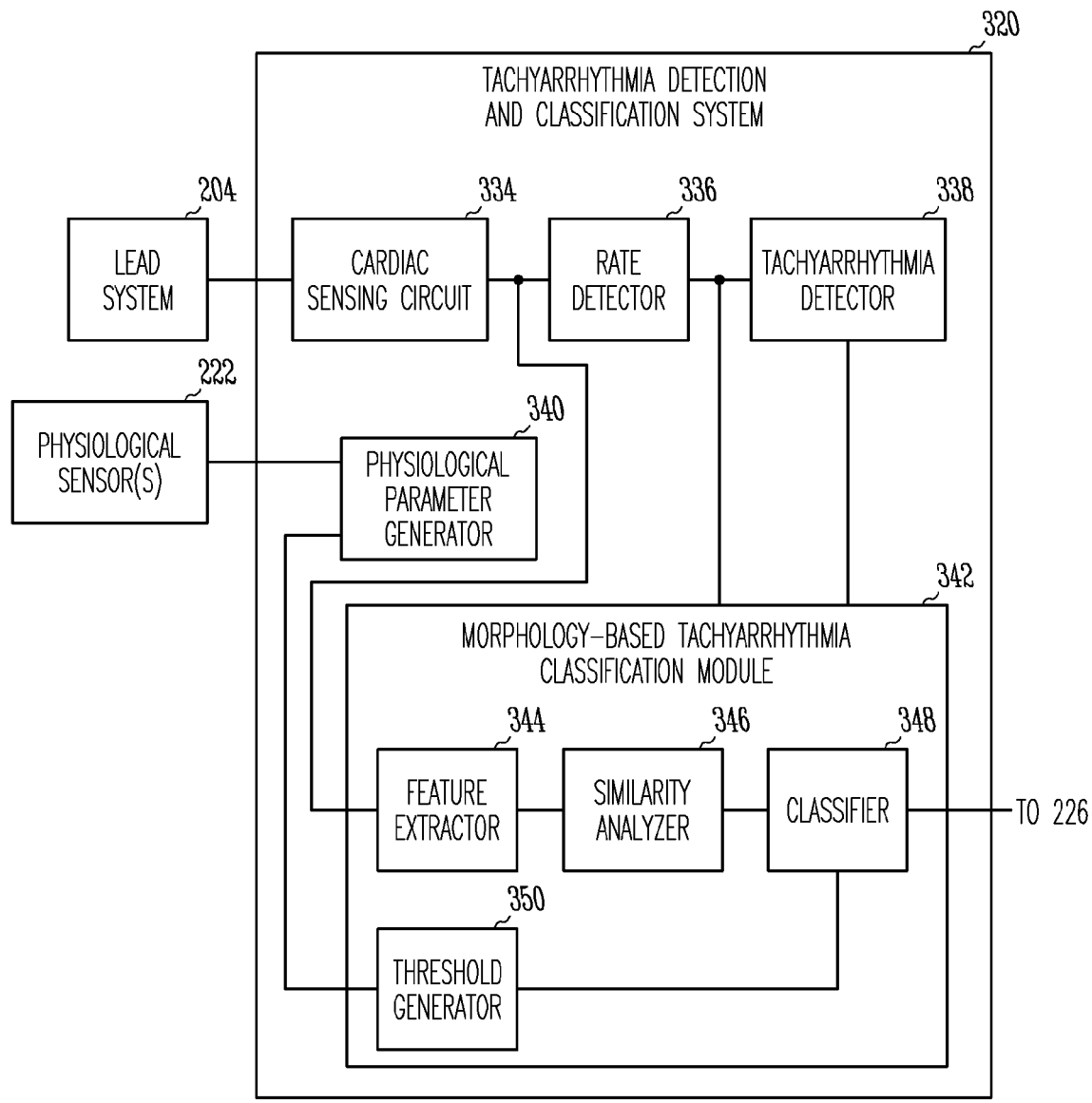
FIG. 3 is a block diagram illustrating a specific embodiment of portions of the CRM system including a tachyarrhythmia detection and classification system coupled to the lead system and the one or more physiological sensors.

FIG. 3 is a block diagram illustrating a specific embodiment of portions of CRM system 100, including a tachyarrhythmia detection and classification system 320 coupled to lead system 204 and physiological sensor(s) 222. Tachyarrhythmia detection and classification system 320 is a specific embodiment of tachyarrhythmia detection and classification system 120 and includes a cardiac sensing circuit 334, a rate detector 336, a tachyarrhythmia detector 338, a physiological parameter generator 340, and a morphology-based tachyarrhythmia classification module 342.

Cardiac sensing circuit 334 senses one or more cardiac signals, such as one or more electrograms, through lead system 204. In one embodiment, cardiac sensing circuit 334 is electrically coupled to heart 199 through lead system 204 to sense an atrial electrogram and a ventricular electrogram from the heart. The atrial electrogram includes atrial events, also known as P waves, each indicative of an atrial depolarization. The ventricular electrogram includes ventricular events, also known as R waves, each indicative of a ventricular depolarization.

Rate detector 336 detects a heart rate from a cardiac signal sensed by cardiac sensing circuit 334. In one embodiment, rate detector 336 detects an atrial rate from the atrial electrogram and/or a ventricular rate from the ventricular electrogram. The atrial rate is the frequency of the atrial events. The ventricular rate is the frequency of the ventricular events. In one embodiment, the atrial and ventricular rates are each expressed in beats per minute (bpm), i.e., number of detected atrial or ventricular depolarizations per minute.

Tachyarrhythmia detector 338 detects a tachyarrhythmia episode using the heart rate and one or more tachyarrhythmia detection thresholds. In one embodiment, the tachyarrhythmia is detected when the atrial rate exceeds a predetermined tachyarrhythmia threshold rate. In another embodiment, the tachyarrhythmia is detected when the ventricular rate exceeds a predetermined tachyarrhythmia threshold rate.

Physiological parameter generator 340 derives one or more physiological parameters from the one or more physiological signals sensed by physiological sensor(s) 222. The one or more physiological parameters each indicate a physiological condition that potentially affect the accuracy of a morphology-based tachyarrhythmia classification performed for the purpose of determining a suitable or optimal therapy.

Morphology-based tachyarrhythmia classification module 342 includes a feature extractor 344, a similarity analyzer 346, a classifier 348, and a threshold generator 350. Feature extractor 344 extracts arrhythmic morphological features of an arrhythmic heart beat of the detected tachyarrhythmia episode from a cardiac signal sensed by cardiac sensing circuit 334. Similarity analyzer 346 computes a measure of morphological similarity between the waveform of the arrhythmic heart beat and the waveform of a template heart beat of a known type cardiac rhythm. In one embodiment, similarity analyzer 346 includes a correlation analyzer that computes a correlation coefficient between the arrhythmic morphological features and template morphological features of the template heart beat for each arrhythmic heart beat of a plurality of arrhythmic heart beats of the detected tachyarrhythmia episode. One example for calculating such a correlation coefficient, referred to as a feature correlation coefficient (Fcc), is discussed in U.S. Pat. No. 6,708,058, "NORMAL CARDIAC RHYTHM TEMPLATE GENERATION SYSTEM AND METHOD," assigned to Cardiac Pacemakers, Inc., which is hereby incorporated in its entirety. The measure of similarity (such as the correlation coefficient) is used as a matching score indicative of whether the morphology of the arrhythmic heart beat substantially matches the morphology of the template heart beat. Classifier 348 classifies the detected tachyarrhythmia episode using the values of the measure of similarity calculated for the plurality of arrhythmic heart beats and a dynamically adjustable beat classification threshold (T). If the value of the measure of similarity computed for an arrhythmic heart beat exceeds the beat classification threshold (T), the arrhythmic heart beat is classified as a heart beat of a tachyarrhythmia type having a known morphological relationship with the known type cardiac rhythm (i.e., morphologically matches the template heart beat). The detected tachyarrhythmia episode is then classified by a majority voting of the classified arrhythmic heart beats. Threshold generator 350 adjusts the beat classification threshold (T) using the one or more physiological parameters.

In various embodiments specifically discussed in this document, correlation coefficient is used as a specific example of the measure of similarity between arrhythmic morphological features and template morphological features. However, the present subject matter applies to any measure of similarity that indicates a degree of similarity, matching, or correlation between arrhythmic morphological features of an arrhythmic heart beat and template morphological features of a template heart beat of a known type cardiac rhythm. In various other embodiments, for the purpose of classifying a detected tachyarrhythmia episode by comparing the measure of similarity to a threshold, the correlation coefficient as discussed in this document is replaced by another measure of similarity (other than a correlation coefficient) between arrhythmic morphological features of an arrhythmic heart beat and template morphological features of a template heart beat of a known type cardiac rhythm.

In a specific embodiment, morphology-based tachyarrhythmia classification module 342 classifies a detected tachyarrhythmia episode as one of VT and SVT after the detected tachyarrhythmia episode is first classified as a 1:1 tachyarrhythmia. A tachyarrhythmia is classified as a 1:1 tachyarrhythmia when the atrial rate and the ventricular rate are substantially equal. In one embodiment, morphology-based tachyarrhythmia classification module 342 classifies the detected tachyarrhythmia episode as the 1:1 tachyarrhythmia when the difference between the atrial rate and the ventricular rate is less than a predetermined limit, such as 10 bpm. Subsequently, morphology-based tachyarrhythmia classification module 342 further classifies the 1:1 tachyarrhythmia as one of VT and SVT by performing one or more methods discussed in this document. The known type cardiac rhythm is a normal sinus rhythm (NSR). If the correlation coefficient computed for an arrhythmic heart beat exceeds the beat classification threshold (T), the arrhythmic heart beat is classified as an SVT beat. If a substantial number of the arrhythmic heart beats are classified as SVT beat, the detected tachyarrhythmia episode is classified as an SVT episode.

In another specific embodiment, morphology-based tachyarrhythmia classification module 342 classifies a detected tachyarrhythmia episode as one of VT and SVT when the atrial rate substantially exceeds the ventricular rate, such as by a margin of approximately 10 bpm. The detected tachyarrhythmia episode is classified as one of VT and SVT by performing one or more methods discussed in this document.

In another specific embodiment, morphology-based tachyarrhythmia classification module 342 classifies a detected tachyarrhythmia episode as one of VT and SVT when only ventricular rate is detected (for example, when atrial electrogram is not sensed). This allows discrimination between VT and SVT without sensing an atrial electrogram. The detected tachyarrhythmia episode is classified as one of VT and SVT by performing one or more methods discussed in this document, without a step of comparing the ventricular rate with the atrial rate.

Figure 4:
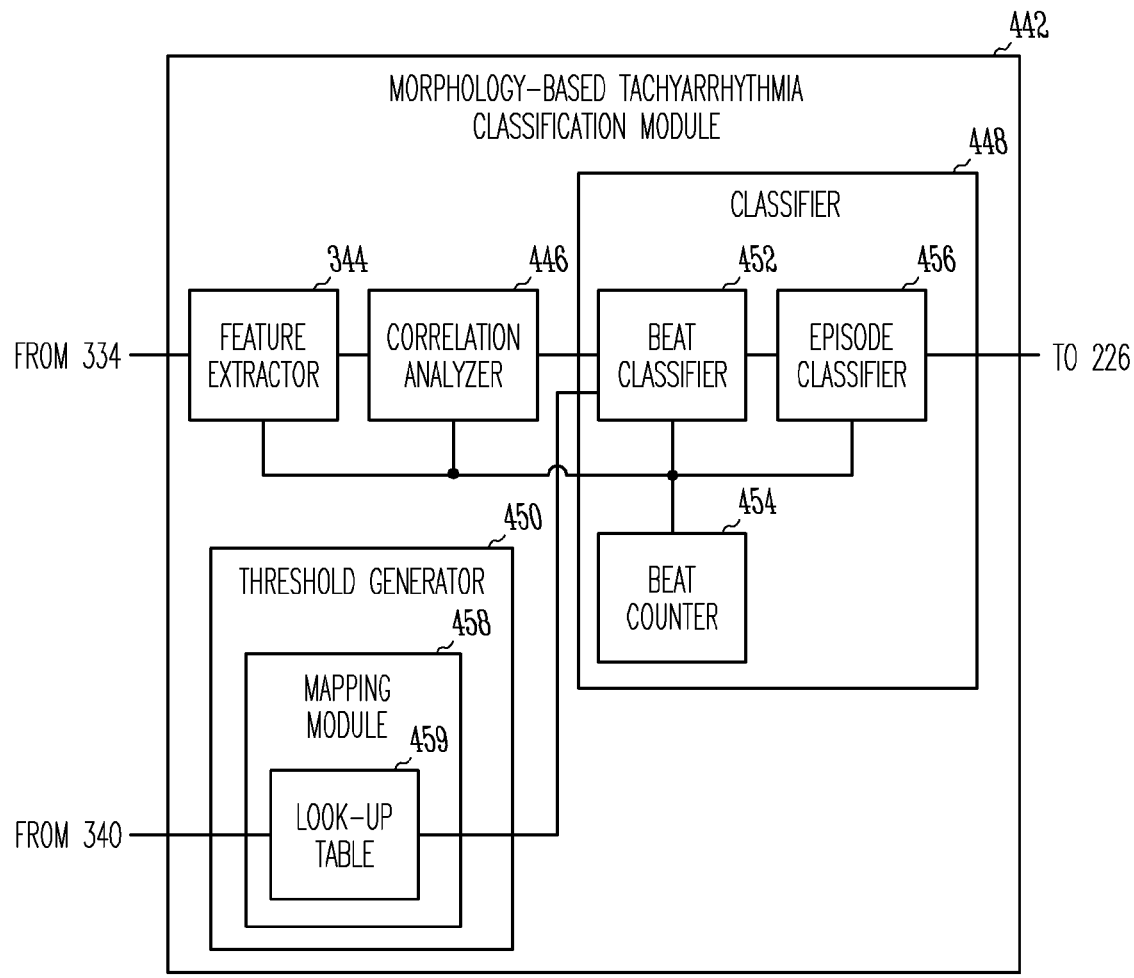
FIG. 4 is a block diagram illustrating an embodiment of a morphology-based tachyarrhythmia classification module of the tachyarrhythmia detection and classification system.

FIG. 4 is a block diagram illustrating an embodiment of a morphology-based tachyarrhythmia classification module 442, which is a specific embodiment of morphology-based tachyarrhythmia classification module 342. Morphology-based tachyarrhythmia classification module 442 includes feature extractor 344, a correlation analyzer 446, a classifier 448, and a threshold generator 450.

Correlation analyzer 446 is a specific embodiment of similarity analyzer 346 and computes the correlation coefficient between the arrhythmic morphological features and the template morphological features. For the purpose of classifying the detected tachyarrhythmia episode, correlation analyzer 446 computes the correlation coefficient for each of a plurality of arrhythmic heart beats of the detected tachyarrhythmia episode.

Classifier 448 is a specific embodiment of classifier 348 and includes a beat classifier 452, a beat counter 454, and an episode classifier 456. Beat classifier 452 includes a beat comparator having a first input receiving the correlation coefficient for each of the predetermined number of arrhythmic heart beats, a second input receiving the beat classification threshold (T), and an output indicating a classification for the each of the plurality of arrhythmic heart beats as one of a first type tachyarrhythmic heart beat and a second type tachyarrhythmic heart beat. Beat counter 454 counts a number of the arrhythmic heart beats classified as the first type tachyarrhythmic heart beat. Episode classifier 456 includes an episode comparator having a first input receiving the number of the arrhythmic heart beats classified as the first type tachyarrhythmic heart beat, a second input receiving an episode classification threshold, and an output indicating a classification of the detected tachyarrhythmia episode one of a first type tachyarrhythmia and a second type tachyarrhythmia. The episode classification threshold specifies a minimum count of the arrhythmic heart beats for the detected tachyarrhythmia episode to be classified as a first type tachyarrhythmia episode by the majority voting.

Threshold generator 450 is a specific embodiment of threshold generator 350 and includes a mapping module 458. Mapping module 458 maps the one or more physiological parameters produced by physiological parameter generator 340 to one of a plurality of predetermined values of the beat classification threshold (T). In one embodiment, as illustrated in FIG. 3, mapping module 458 includes a look-up table 459 that relates the one or more physiological parameters to the plurality of predetermined values of the beat classification threshold (T). In another embodiment, mapping module 458 calculates the beat classification threshold (T) using one or more given equations relating the one or more physiological parameters to the plurality of predetermined values of the beat classification threshold (T).

Figure 5:
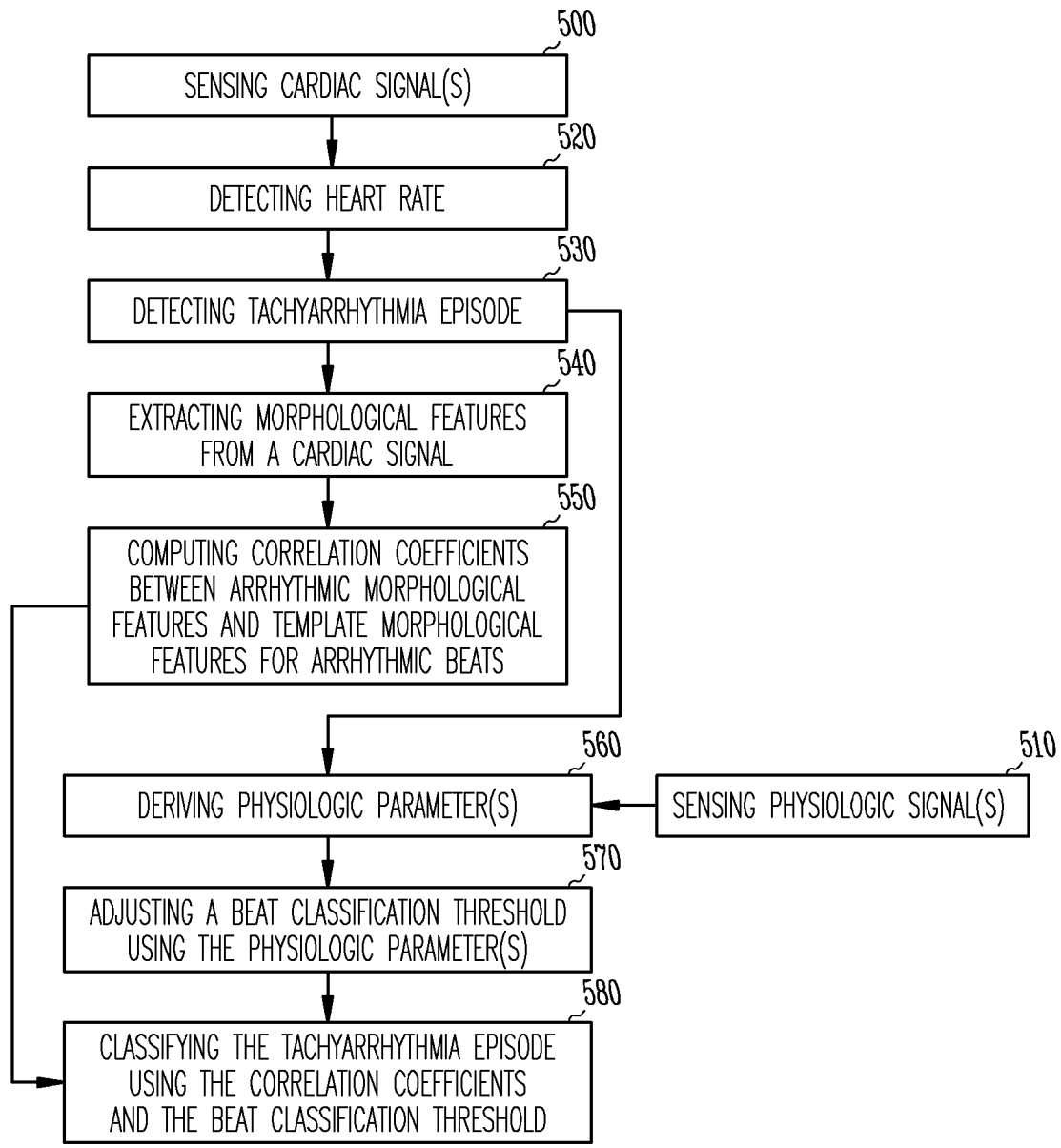
FIG. 5 is a flow chart illustrating an embodiment of a method for morphology-based tachyarrhythmia classification using a dynamically adjustable beat classification threshold.

FIG. 5 is a flow chart illustrating an embodiment of a method for morphology-based tachyarrhythmia classification using a dynamically adjustable beat classification threshold. In one embodiment, the method is applied to operate an ICD, such as ICD 101.

One or more cardiac signals are sensed at 500. A heart rate is detected from one of the sensed one or more cardiac signals at 520. A tachyarrhythmia episode is detected using the heart rate and one or more tachyarrhythmia detection thresholds at 530.

After a tachyarrhythmia episode is detected, arrhythmic morphological features are extracted from an arrhythmic waveform associated with an arrhythmic heart beat of the tachyarrhythmia episode at 540. The arrhythmic waveform is a portion of one of the sensed one or more cardiac signals. The arrhythmic morphological features are points in the cardiac signal that have morphological characteristics allowing discrimination between two or more types of tachyarrhythmias. A correlation coefficient is computed between the arrhythmic morphological features and template morphological features of a template heart beat of a known type cardiac rhythm at 550, for each arrhythmic heart beat of a plurality of arrhythmic heart beats. In one embodiment, the correlation coefficient is a feature correlation coefficient (Fcc). In one embodiment, the template heart beat represents a heart beat of the NSR. In one embodiment, the template morphological features are collected from the template heart beat and stored. This includes recording timing and other quantitative information, such as amplitudes, associated with the features. In one specific embodiment, the feature collection is repeated for a plurality of template heart beats, and the timing and other quantitative information associated with the features are averages calculated over the plurality of template heart beats. For classifying the detected tachyarrhythmia episode, arrhythmic morphological features are extracted from the arrhythmic heart beat by temporal correspondence with the template morphological features of the template heart beat at 540. A set of template morphological features and a set of corresponding arrhythmic morphological features are thus collected for the correlation analysis that follows. In another embodiment, a template waveform is stored. For discriminating the detected tachyarrhythmia episode, arrhythmic morphological features are collected from the arrhythmic heart beat. Then, template morphological features are extracted from the stored template waveform at the locations temporally corresponding to the locations of the arrhythmic morphological features on the arrhythmic waveform at 540. A set of template morphological features and a set of arrhythmic morphological features are thus collected for the correlation analysis that follows. In one specific embodiment, the template waveform is averaged over a plurality of template heart beats.

One or more physiological signals are sensed at 510. After the tachyarrhythmia episode is detected at 530, one or more physiological parameters are derived from the one or more physiological signals at 560. A beat classification threshold (T) is adjusted using the one or more physiological parameters at 570. In one embodiment, the one or more physiological parameters are mapped to one of a plurality of predetermined values of the beat classification threshold (T). In a specific embodiment, the mapping is performed using a lookup table relating the one or more physiological parameters to the plurality of predetermined values of the beat classification threshold (T).

The tachyarrhythmia episode is classified using the correlation coefficients calculated for a predetermined number of arrhythmic heart beats and a dynamically adjustable beat classification threshold (T) at 580. In one embodiment, the correlation coefficient for each of the predetermined number of arrhythmic heart beats is compared to the beat classification threshold (T). A classification for each of the predetermined number of arrhythmic heart beats is indicated as one of a first type tachyarrhythmic heart beat and a second type tachyarrhythmic heart beat. For example, to classify a tachyarrhythmia episode as one of VT and SVT using an NSR beat as the template heart beat, a heart beat is classified as an SVT beat if the associated correlation coefficient exceeds the beat classification threshold (T), indicating the beat as substantially morphologically correlated to the NSR beat. A number of the arrhythmic heart beats classified as the first type tachyarrhythmic heart beat is counted. The count of the arrhythmic heart beats classified as the first type tachyarrhythmic heart beat is compared to an episode classification threshold. The detected tachyarrhythmia episode is classified as one of a first type tachyarrhythmia and a second type tachyarrhythmia depending on the outcome of the comparison. In one embodiment, the detected tachyarrhythmia episode is classified by a majority voting. That is, the tachyarrhythmia episode is classified as the first type tachyarrhythmia if a majority of the analyzed arrhythmic heart beats are classified as the heart beats of the first type tachyarrhythmia. In one specific embodiment, 80% (such as 8 out of 10 analyzed arrhythmic heart beats) is considered as the majority. For example, to classify a tachyarrhythmia episode as one of VT and SVT using an NSR beat as the template heart beat, if 8 out of 10 arrhythmic heart beats are classified as VT beats, the tachyarrhythmia episode is classified as a VT episode. Otherwise, it is classified as an SVT episode. In another specific embodiment, 60% is considered as the majority.

In one embodiment, delivery of one or more therapies is controlled using the classification of the tachyarrhythmia episode. Examples of such therapies include ATP therapy and cardioversion/defibrillation therapy. The effectiveness of each therapy is verified following the delivery of the each therapy to determine whether another delivery of the same therapy or a delivery of a more aggressive therapy is necessary.

Figure 6:
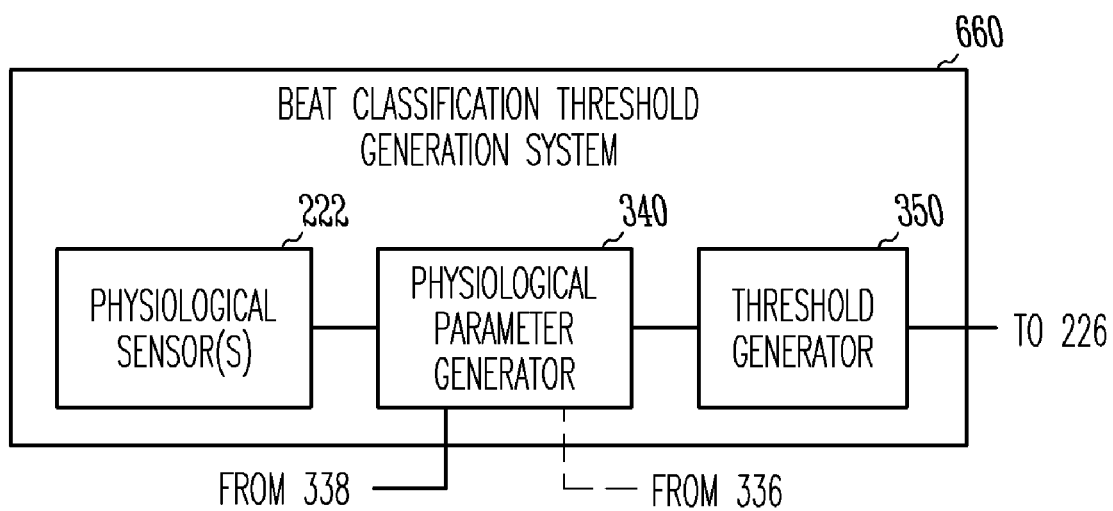
FIG. 6 is a block diagram illustrating an embodiment of a beat classification threshold generation system.

FIG. 6 is a block diagram illustrating an embodiment of a beat classification threshold generation system 660, what represents portions of ICD 101 that provide for the dynamic adjustment of the beat classification threshold (T). Beat classification threshold generation system 660 includes physiologic sensor(s) 222, physiological parameter generator 340, and threshold generator 350. For the purpose of illustration, but not for the purpose of restriction, various embodiments for adjusting the beat classification threshold (T) using one or more physiological parameters are discussed below in Examples 1-4, with reference to FIGS. 7-14.

Example 1

Beat Classification Threshold Adjustment Using Single Hemodynamic Signal

In one embodiment, the beat classification threshold (T) is dynamically adjusted using a hemodynamic stability parameter (S) indicative of a level of hemodynamic stability. The hemodynamic stability parameter (S) is derived from a hemodynamic signal indicative of hemodynamic performance and is a measure of the stability of a hemodynamic parameter representative of an attribute of the hemodynamic signal.

Figure 7:
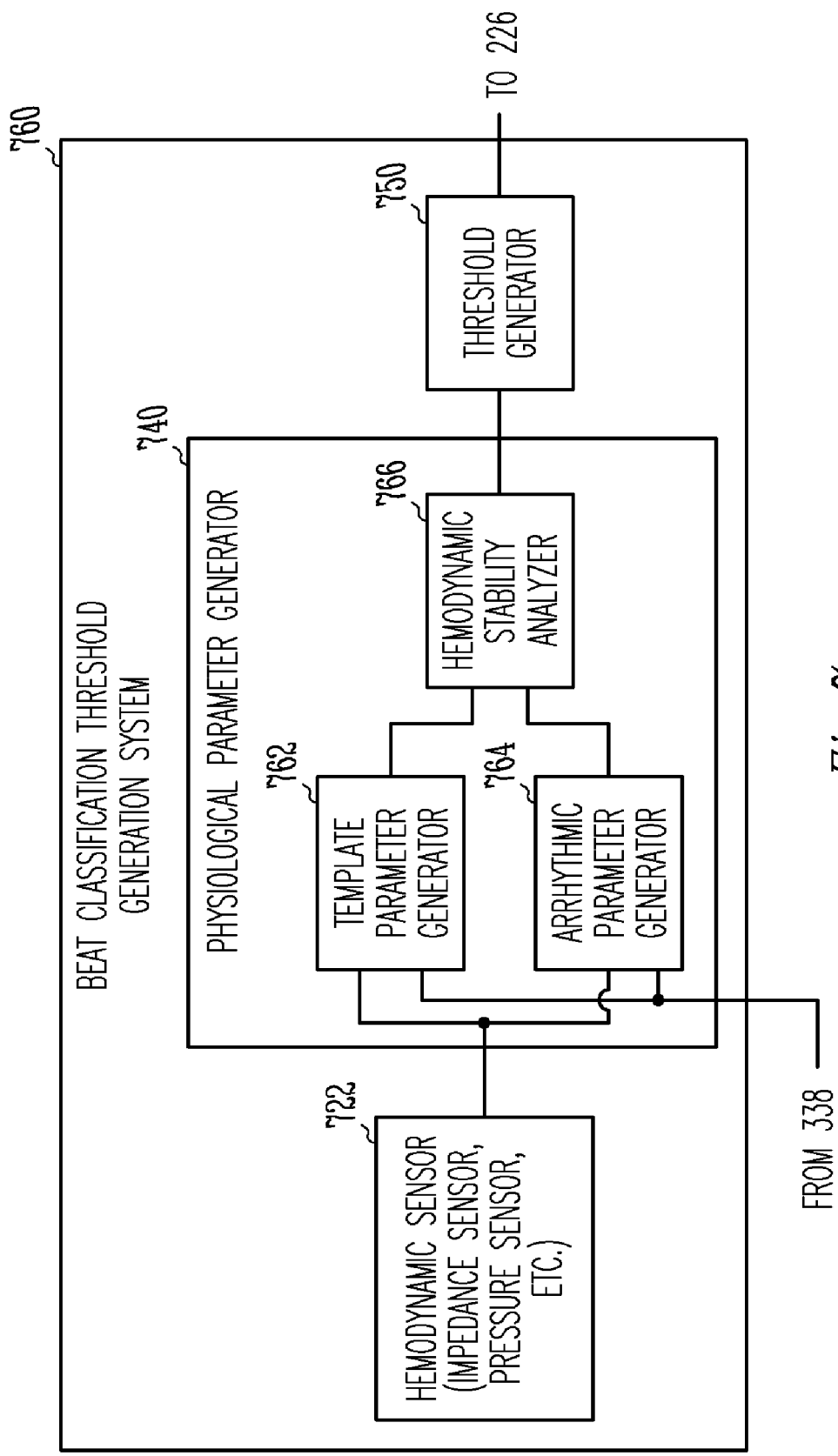
FIG. 7 is a block diagram illustrating a specific embodiment of the beat classification threshold generation system.

FIG. 7 is a block diagram illustrating an embodiment of a beat classification threshold generation system 760, which is a specific embodiment of beat classification threshold generation system 660. Beat classification threshold generation system 760 includes a hemodynamic sensor 722, a physiological parameter generator 740, and a threshold generator 750.

Hemodynamic sensor 722 is a specific embodiment of physiological sensor(s) 222 and senses the hemodynamic signal. Physiological parameter generator 740 is a specific embodiment of physiological parameter generator 340 and derives the hemodynamic stability parameter (S) from the hemodynamic signal. Physiological parameter generator 740 includes a template parameter generator 762, an arrhythmic parameter generator 764, and a hemodynamic stability analyzer 766. Template parameter generator 762 produces a template hemodynamic parameter ($H_T$). In one embodiment, the template hemodynamic parameter ($H_T$) is measured from the hemodynamic signal when the patient's hemodynamic performance is determined to be normal or stable, such as during the NSR. In another embodiment, the template hemodynamic parameter ($H_T$) is empirically estimated from the hemodynamic signal during hemodynamically tolerable tachyarrhythmia, such as tachyarrhythmia caused by exercise. Arrhythmic parameter generator 764 measures an arrhythmic hemodynamic parameter ($H_A$) from the hemodynamic signal during the detected tachyarrhythmia episode. Hemodynamic stability analyzer 766 produces the hemodynamic stability parameter (S) as a function of the template hemodynamic parameter ($H_T$) and the arrhythmic hemodynamic parameter ($H_A$).

In one embodiment, hemodynamic stability analyzer 766 computes a change ($\delta$), which is a ratio of the difference between the arrhythmic hemodynamic parameter ($H_A$) and the template hemodynamic parameter ($H_T$) to the template hemodynamic parameter ($H_T$). That is, $$\delta = (H_T - H_A)H_T. \quad [1]$$

Then, hemodynamic stability analyzer 766 produces the hemodynamic stability parameter (S) as a function of the change ($\delta$). In one embodiment, the hemodynamic stability parameter (S) is assigned one of a plurality of predetermined values ($S_i$) each representing a level of hemodynamic stability. For example:

$$S = \begin{cases} S_1 & a < \delta < 1; \\ S_2 & b < \delta < a; \\ S_3 & c < \delta < b; \\ S_4 & \delta < c, \end{cases} \quad [2]$$

where $S_1$ indicates a very stable hemodynamic performance, $S_2$ indicates a somewhat stable hemodynamic performance, $S_3$ indicates a somewhat unstable hemodynamic performance, and $S_4$ indicates a very unstable hemodynamic performance. Threshold values a, b, and c are empirically determined. In one embodiment, the change ($\delta$) is expressed as a percentage change, and a, b, and c are each given as a percentage.

Threshold generator 750 is a specific embodiment of threshold generator 350 and adjusts the beat classification threshold (T) using the hemodynamic stability parameter (S) produced by hemodynamic stability analyzer 766. In one embodiment, threshold generator 750 maps each value ($S_i$) of the hemodynamic stability parameter (S) to a predetermined value ($T_i$) of the beat classification threshold (T). In one embodiment, the predetermined values ($T_i$) of the beat classification threshold (T) are each determined by using the equation:

$$T_i = T_0 + (i-1) \cdot \alpha, \quad [3]$$

where $T_0$ is a baseline threshold corresponding to a very stable hemodynamic performance, i is the level of the hemodynamic stability ($1 \leq i \leq 4$ as in the example pf Equation [2]), and $\alpha$ is an empirically determined step size of positive value. In a specific embodiment, a equals 0.01. In a morphological analysis in which a calculated correlation coefficient has a value between 0 and 1, because $T_i$ cannot be greater than 1, $\alpha$ is limited to $(1-T_0)/4$. In a specific embodiment, $T_0$ equals 0.9 or lower, and $\alpha$ is between 0 and 0.015.

In a specific embodiment, the hemodynamic signal is an impedance signal indicative of a transthoracic impedance or a cardiac impedance. Hemodynamic sensor 722 includes an impedance sensor to sense the impedance signal. Physiological parameter generator 740 derives the hemodynamic stability parameter (S) from the impedance signal. In one embodiment, physiological parameter generator 740 includes a stroke impedance detector to measure a stroke impedance ($\Delta Z$) from the impedance signal. The stroke impedance ($\Delta Z$) is the difference between a maximum impedance ($Z_{max}$) and a minimum impedance ($Z_{min}$) over a cardiac cycle. The template hemodynamic parameter ($H_T$) is a template stroke impedance ($\Delta Z_T$). The arrhythmic hemodynamic parameter ($H_A$) is an arrhythmic stroke impedance ($\Delta Z_A$). The hemodynamic stability parameter (S) is a function of the template stroke impedance ($\Delta Z_T$) and the arrhythmic stroke impedance ($\Delta Z_A$).

In another specific embodiment, the hemodynamic signal is a pressure signal indicative of an arterial pressure. Hemodynamic sensor 722 includes a pressure sensor to sense the pressure signal. In one embodiment, the pressure signal is a pulmonary artery pressure (PAP) signal indicative of PAP, and the pressure sensor is an implantable PAP sensor. Physiological parameter generator 740 derives the hemodynamic stability parameter (S) from the pressure signal. In one embodiment, physiological parameter generator 740 includes a pressure detector to measure a pressure (P) from the pressure signal. Examples of the pressure (P) include a pulse pressure (the difference between the systolic pressure and diastolic pressure) and a pressure measured at a predetermined point in a cardiac cycle. The template hemodynamic parameter ($H_T$) is a template pressure ($P_T$), which is a pressure value estimated for the heart rate detected during the detected tachyarrhythmia episode. Template parameter generator 762 produces the template pressure ($P_T$) as a function of the heart rate detected during the detected tachyarrhythmia episode. In one embodiment, the function for producing the template pressure ($P_T$) is empirically derived from data collected from a patient population. The arrhythmic hemodynamic parameter ($H_A$) is an arrhythmic pressure ($P_A$). The hemodynamic stability parameter (S) is a function of the template pressure ($P_T$) and the arrhythmic pressure ($P_A$).

In various other specific embodiments, the hemodynamic signal includes any signal indicative of hemodynamic performance. Examples of such a hemodynamic signal include a signal indicative of blood flow, a signal indicative of heart sounds, an oximetry signal indicative of blood oxygenation, a plethysmographic signal indicative of cardiac output, a respiratory signal, and a cardiac contractility signal (such as an endocardial acceleration signal). Accordingly, examples of hemodynamic sensor 722 include a flow sensor to sense the signal indicative of blood flow, a heart sound sensor to sense the signal indicative of heart sounds (such as an accelerometer or a microphone), a pulse oximetry sensor to sense the oximetry signal, a photoplethysmography sensor to sense the plethysmographic signal, a respiratory sensor to sense the respiratory signal, and a cardiac contractility sensor to sense the cardiac contractility signal (such as an endocardial accelerometer to sense the endocardial acceleration signal). Physiological parameter generator 740 derives the hemodynamic stability parameter (S) from any one of these signals.

Figure 8:
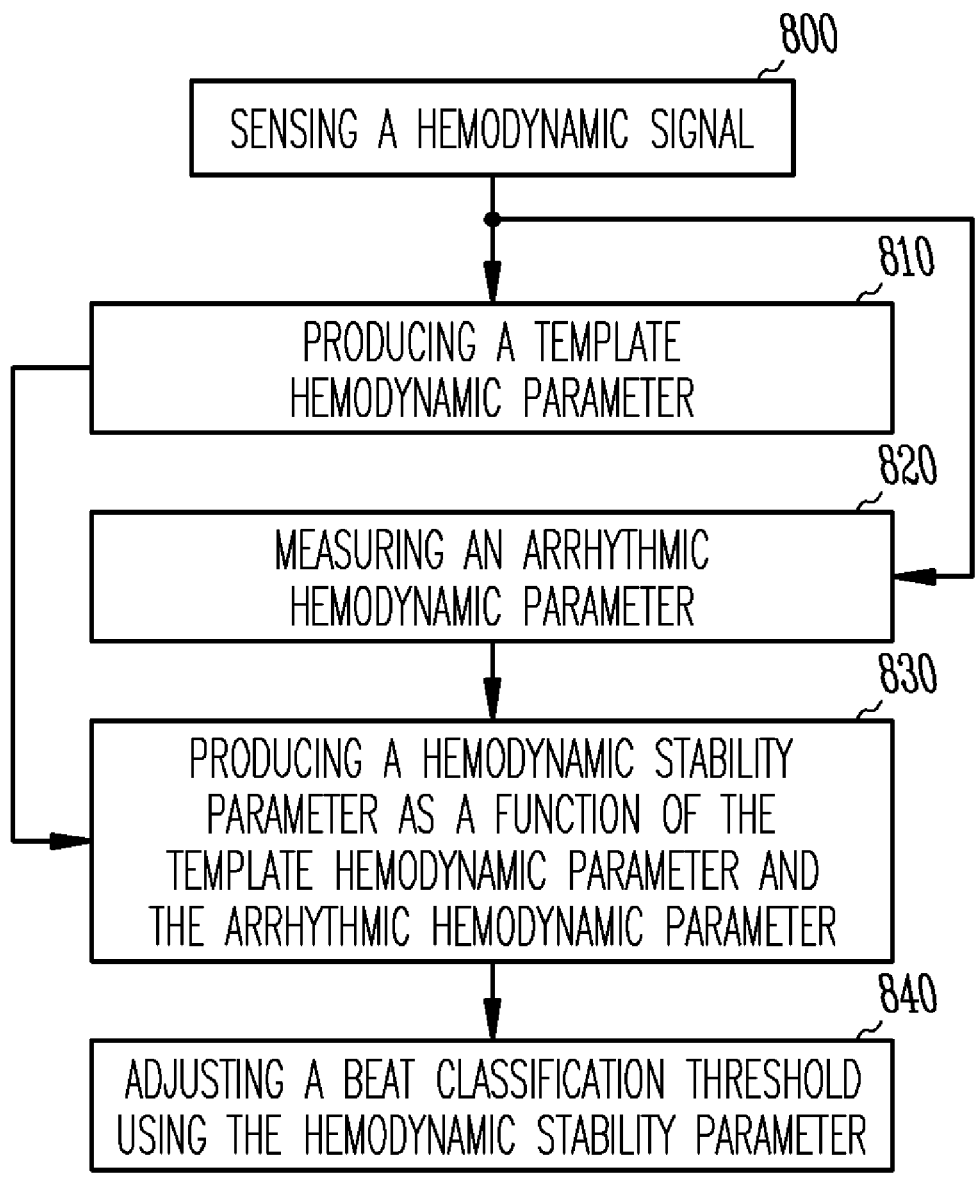
FIG. 8 is a flow chart illustrating a specific embodiment of a method for adjusting the beat classification threshold.

FIG. 8 is a flow chart illustrating a specific embodiment of a method for adjusting the beat classification threshold (S). In one embodiment, the method is performed by beat classification threshold generation system 760.

A hemodynamic signal is sensed at 800. Examples of the hemodynamic signal include an impedance signal, a blood pressure signal, a signal indicative of blood flow, a signal indicative of heart sounds, an oximetry signal indicative of blood oxygenation, a plethysmographic signal indicative of cardiac output, a respiratory signal, and a cardiac contractility signal (such as an endocardial acceleration signal). A template hemodynamic parameter ($H_T$) is produced at 810. In one embodiment, the template hemodynamic parameter ($H_T$) is measured during a period when the patient's hemodynamic performance is known to be normal or stable, such as during the NSR. In another embodiment, the template hemodynamic parameter ($H_T$) is empirically estimated from the hemodynamic signal during hemodynamically tolerable tachyarrhythmia. An arrhythmic hemodynamic parameter ($H_A$) is measured from the hemodynamic signal during the detected tachyarrhythmia episode at 820.

The hemodynamic stability parameter (S) is produced as a function of the template hemodynamic parameter ($H_T$) and the arrhythmic hemodynamic parameter ($H_A$) at 830. In one embodiment, a ratio of the difference between the arrhythmic hemodynamic parameter ($H_A$) and the template hemodynamic parameter ($H_T$) to the template hemodynamic parameter ($H_T$) is computed using Equation [1], and the hemodynamic stability parameter (S) is produced as a function of that ratio using Equation [2]. The beat classification threshold (T) is adjusted using the hemodynamic stability parameter (S) at 840. In one embodiment, each value ($S_i$) of the hemodynamic stability parameter (S) is mapped to one of predetermined values ($T_i$) of the beat classification threshold (T).

In a specific embodiment, the hemodynamic signal is an impedance signal indicative of a transthoracic impedance or a cardiac impedance. The template hemodynamic parameter ($H_T$) and the arrhythmic hemodynamic parameter ($H_A$) are each a stroke impedance ($\Delta Z$) measured from the impedance signal. The stroke impedance is the difference between a maximum impedance ($Z_{max}$) and a minimum impedance ($Z_{min}$) over a cardiac cycle. A template stroke impedance ($\Delta Z_T$) is produced as the template hemodynamic parameter ($H_T$) at 810. An arrhythmic stroke impedance ($\Delta Z_A$) is measured as the arrhythmic hemodynamic parameter ($H_A$) at 820.

In another specific embodiment, the hemodynamic signal is a pressure signal indicative of an arterial pressure, such as a PAP signal indicative of PAP. The template hemodynamic parameter ($H_T$) and the arrhythmic hemodynamic parameter ($H_A$) are each a pressure (P) measured from the pressure signal, such as a pulse pressure or a pressure value at a predetermined point in a cardiac cycle. A template pressure ($P_T$) is produced as the template hemodynamic parameter ($H_T$) at 810. The template pressure ($P_T$) is a pressure value estimated for the heart rate detected during the detected tachyarrhythmia episode. In one embodiment, the template pressure ($P_T$) is produced as a given function of the heart rate detected during the detected tachyarrhythmia episode. In a specific embodiment, the function for producing the template pressure ($P_T$) is empirically derived from data collected from a patient population. An arrhythmic pressure ($P_A$) is measured as the arrhythmic hemodynamic parameter ($H_A$) at 820.

Example 2

Beat Classification Threshold Adjustment Using Multiple Hemodynamic Signals

In one embodiment, the beat classification threshold (T) is dynamically adjusted using a hemodynamic stability parameter (S) indicative of a level of hemodynamic stability. The hemodynamic stability parameter (S) is derived from two or more hemodynamic signals each indicative of hemodynamic performance. While an embodiment with two hemodynamic signals is specifically discussed as an example, three or more hemodynamic signals may be used to derive the hemodynamic stability parameter (S) using similar approaches.

Figure 9:
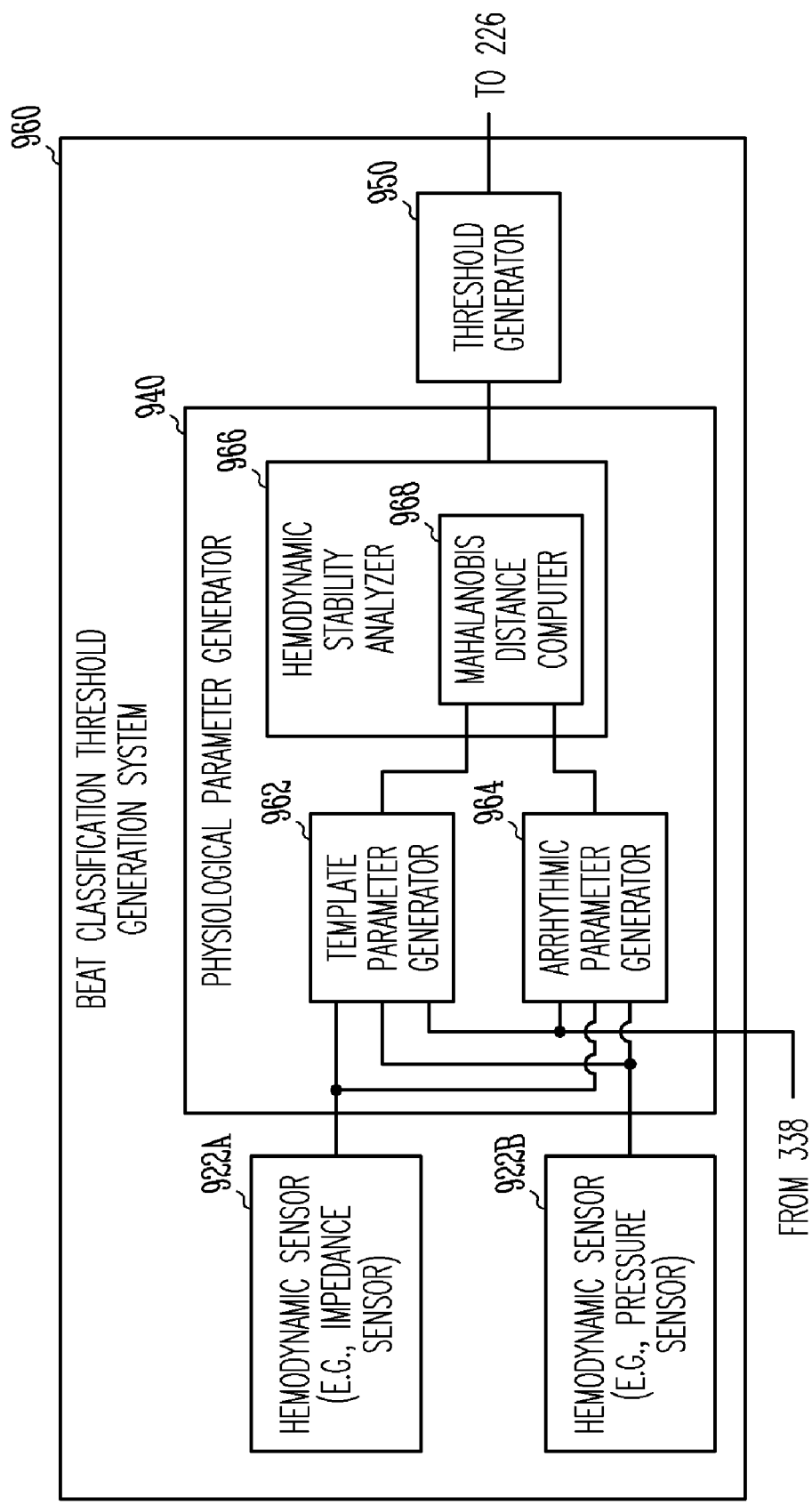
FIG. 9 is a block diagram illustrating another specific embodiment of the beat classification threshold generation system.

FIG. 9 is a block diagram illustrating another specific embodiment of a beat classification threshold generation system 960, which is a specific embodiment of beat classification threshold generation system 660. Beat classification threshold generation system 960 includes hemodynamic sensors 922A and 922B, a physiological parameter generator 940, and a threshold generator 950.

Hemodynamic sensors 922A and 922B are a specific embodiment of physiological sensor(s) 222. Hemodynamic sensor 922A senses a first hemodynamic signal indicative of hemodynamic performance. Hemodynamic sensor 922B senses a second hemodynamic signal indicative of hemodynamic performance. Physiological parameter generator 940 is a specific embodiment of physiological parameter generator 340 and derives the hemodynamic stability parameter (S) from the first and second hemodynamic signals sensed by hemodynamic sensors 922A and 922B. Physiological parameter generator 940 includes a template parameter generator 962, an arrhythmic parameter generator 964, and a hemodynamic stability analyzer 966. Template parameter generator 962 produces a first template hemodynamic parameter ($H_{1T}$) for the first hemodynamic signal, a second template hemodynamic parameter ($H_{2T}$) for the second hemodynamic signal, and a template parameter vector $U_T = [H_{1T}, H_{2T}]$. Such template parameters are produced from the first and second hemodynamic signals sensed when the patient's hemodynamic performance is normal or stable, such as during the NSR, or at an elevated heart rate during a tachyarrhythmia from normal stage. In one embodiment, template parameter generator 962 also produces a first variance (var($H_{1T}$)) of the first template hemodynamic parameter ($H_{1T}$) for the first hemodynamic signal, a second variance (var($H_{2T}$)) of the second template hemodynamic parameter ($H_{2T}$) for the second hemodynamic signal. Arrhythmic parameter generator 964 measures a first arrhythmic hemodynamic parameter ($H_{1A}$) from the first hemodynamic signal during the detected tachyarrhythmia episode and a second arrhythmic hemodynamic parameter ($H_{2A}$) from the second hemodynamic signal during the detected tachyarrhythmia episode, and produces an arrhythmic parameter vector $U_A = [H_{1A}, H_{2A}]$. Hemodynamic stability analyzer 966 produces the hemodynamic stability parameter (S) as a function of the template parameter vector ($U_T$) and the arrhythmic parameter vector ($U_A$), i.e., as a function of the first template hemodynamic parameter ($H_{1T}$), the second template hemodynamic parameter ($H_{2T}$), the first arrhythmic hemodynamic parameter ($H_{1A}$), and the second arrhythmic hemodynamic parameter ($H_{2A}$).

In one embodiment, hemodynamic stability analyzer 966 compute a change ($\delta$) between the template parameter vector ($U_T$) and the arrhythmic parameter vector ($U_A$) and produces the hemodynamic stability parameter (S) as a function of the change ($\delta$). In one embodiment, the change ($\delta$) is a Mahalanobis distance from the arrhythmic parameter vector ($U_A$) to the template parameter vector ($U_T$). As illustrated in FIG. 9, hemodynamic stability analyzer 966 includes a Mahalanobis distance computer to compute the change ($\delta$) using the equation:

$$\delta = (U_A - U_T)\Sigma^{-1}(U_A - U_T)^T, \qquad [4]$$

where $\Sigma^{-1}$ is the inverse of the covariance matrix $\Sigma$ of the arrhythmic parameter vector ($U_A$). In a specific embodiment, a simplified $\Sigma^{-1}$ is used. The simplified $\Sigma^{-1}$ ignores the cross-correlation between the first and second hemodynamic signals, as follows:

$$\Sigma^{-1} = \begin{bmatrix} 1/\text{var}(H_{1T}) & 0 \\ 0 & 1/\text{var}(H_{2T}) \end{bmatrix}, \qquad [5]$$

where var($H_{1T}$) is the variance of the first template hemodynamic parameter ($H_{1T}$), and var($H_{2T}$) is the variance of the second template hemodynamic parameter ($H_{1T}$). Then, hemodynamic stability analyzer 966 produces the hemodynamic stability parameter (S) as a function of the change ($\delta$). In one embodiment, the hemodynamic stability parameter (S) is assigned one of a plurality of predetermined values ($S_i$) each representing a level of hemodynamic stability using Equation [2] as discussed above in Example 1.

Threshold generator 950 is a specific embodiment of threshold generator 350 and adjusts the beat classification threshold (T) using the hemodynamic stability parameter (S) produced by hemodynamic stability analyzer 966. In one embodiment, threshold generator 950 maps each value ($S_i$) of the hemodynamic stability parameter (S) to a predetermined value ($T_i$) of the beat classification threshold (T). In one embodiment, the predetermined values ($T_i$) of the beat classification threshold (T) are each determined by using Equation [3] as discussed above in Example 1.

In a specific embodiment, the first hemodynamic signal is an impedance signal indicative of a transthoracic impedance or a cardiac impedance, and the second hemodynamic signal is a pressure signal indicative of an arterial pressure. Hemodynamic sensor 922A includes an impedance sensor to sense the impedance signal. Hemodynamic sensor 922B includes a pressure sensor to sense the pressure signal. In one embodiment, the pressure signal is a PAP signal indicative of PAP, and the pressure sensor is a PAP sensor. Physiological parameter generator 940 derives the hemodynamic stability parameter (S) from the impedance signal and the pressure signal. In one embodiment, physiological parameter generator 940 includes a stroke impedance detector and a pressure detector. The stroke impedance detector measures a stroke impedance ($\Delta Z$) from the impedance signal. The stroke impedance is the difference between a maximum impedance ($Z_{max}$) and a minimum impedance ($Z_{min}$) over a cardiac cycle. The first template hemodynamic parameter ($H_{1T}$) is a template stroke impedance ($\Delta Z_T$). The first arrhythmic hemodynamic parameter ($H_{1A}$) is an arrhythmic stroke impedance ($\Delta Z_A$). The pressure detector measures a pressure (P) from the pressure signal, such as a pulse pressure or a pressure at a predetermined point in a cardiac cycle. The second template hemodynamic parameter ($H_{2T}$) is a template pressure ($P_T$) being a pressure value estimated for the heart rate detected during the detected tachyarrhythmia episode. Template parameter generator 962 produces the template pressure ($P_T$) as a function of the heart rate detected during the detected tachyarrhythmia episode. In one embodiment, the function for producing the template pressure ($P_T$) is derived from data collected from a patient population. The second arrhythmic hemodynamic parameter ($H_{2A}$) is an arrhythmic pressure ($P_A$). The hemodynamic stability parameter (S) is a function of the template stroke impedance ($\Delta Z_T$), the arrhythmic stroke impedance ($\Delta Z_A$), the template pressure ($P_T$), and the arrhythmic pressure ($P_A$).

Figure 10:
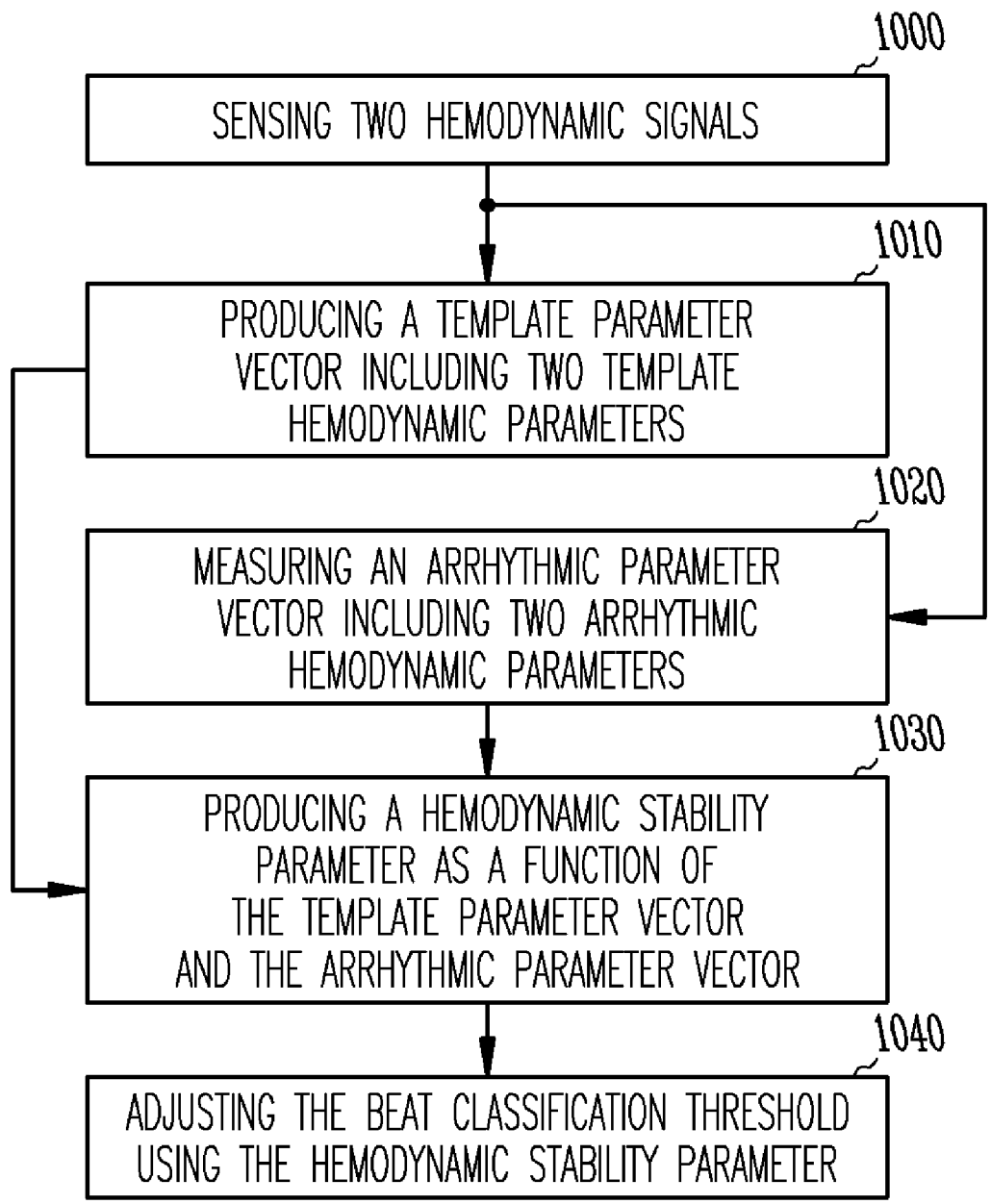
FIG. 10 is a flow chart illustrating another specific embodiment of the method for adjusting the beat classification threshold.

FIG. 10 is a flow chart illustrating another specific embodiment of the method for adjusting the beat classification threshold. In one embodiment, the method is performed by beat classification threshold generation system 960.

Two hemodynamic signals, or first and second hemodynamic signals, are sensed at 1000. A template parameter vector including two template hemodynamic parameters is produced at 1010. This includes producing a first template hemodynamic parameter ($H_{1T}$) for the first hemodynamic signal, a second template hemodynamic parameter ($H_{2T}$) for the second hemodynamic signal, and a template parameter vector $U_T=[H_{1T}, H_{2T}]$. In one embodiment, a first variance (var($H_{1T}$)) of the first template hemodynamic parameter ($H_{1T}$) for the first hemodynamic signal and a second variance (var($H_{2T}$)) of the second template hemodynamic parameter ($H_{2T}$) for the second hemodynamic signal are also produced. An arrhythmic parameter vector including two arrhythmic hemodynamic parameters is measured at 1020. This includes measuring a first arrhythmic hemodynamic parameter ($H_{1A}$) from the first hemodynamic signal during the detected tachyarrhythmia episode and a second arrhythmic hemodynamic parameter ($H_{2A}$) from the second hemodynamic signal during the detected tachyarrhythmia episode, and producing an arrhythmic parameter vector $U_A=[H_{1A}, H_{2A}]$.

The hemodynamic stability parameter (S) is produced as a function of the template parameter vector ($U_T$) and the arrhythmic parameter vector ($U_A$) at 1030. In one embodiment, a change ($\delta$) between the template parameter vector ($U_T$) and the arrhythmic parameter vector ($U_A$) is computed as a Mahalanobis distance from the arrhythmic parameter vector ($U_A$) to the template parameter vector ($U_T$) using Equations [4] and [5], and the hemodynamic stability parameter (S) is produced as a function of that ratio using Equation [2]. The beat classification threshold (T) is adjusted using the hemodynamic stability parameter (S) at 1040. In one embodiment, each value ($S_i$) of the hemodynamic stability parameter (S) is mapped to a predetermined value ($T_i$) of the beat classification threshold (T).

In a specific embodiment, the first hemodynamic signal is an impedance signal indicative of a transthoracic impedance or a cardiac impedance, and the second hemodynamic signal is a pressure signal indicative of an arterial pressure. A stroke impedance ($\Delta Z$) is measured from the impedance signal. The stroke impedance is a difference between a maximum impedance ($Z_{max}$) and a minimum impedance ($Z_{min}$) over a cardiac cycle. A template stroke impedance ($\Delta Z_T$) is produced as the first template hemodynamic parameter ($H_{1T}$) at 1010. An arrhythmic stroke impedance ($\Delta Z_A$) is produced as the first arrhythmic hemodynamic parameter ($H_{1A}$) at 1020. A pressure (P) is measured from the pressure signal. Examples of the pressure include a pulse pressure and a pressure at a predetermined point in a cardiac cycle. A template pressure ($P_T$) is produced as the second template hemodynamic parameter ($H_{2T}$) at 1010. The template pressure ($P_T$) is a pressure value estimated for the heart rate detected during the detected tachyarrhythmia episode. In one embodiment, the template pressure ($P_T$) is produced as a given function of the heart rate detected during the detected tachyarrhythmia episode. In a specific embodiment, the function for producing the template pressure ($P_T$) is derived from data collected from a patient population. An arrhythmic pressure ($P_A$) is measured as the second arrhythmic hemodynamic parameter ($H_{2A}$) at 1020.

Example 3

Beat Classification Threshold Adjustment Using Hemodynamic and Activity Signals

In one embodiment, the beat classification threshold (T) is dynamically adjusted using a hemodynamic stability parameter (S) indicative of a level of hemodynamic stability and an activity parameter (A) indicative of an activity level. The hemodynamic stability parameter (S) is derived from one or more hemodynamic signals each indicative of hemodynamic performance. The activity parameter (A) is derived from an activity signal indicative of a physical activity level.

Figure 11:
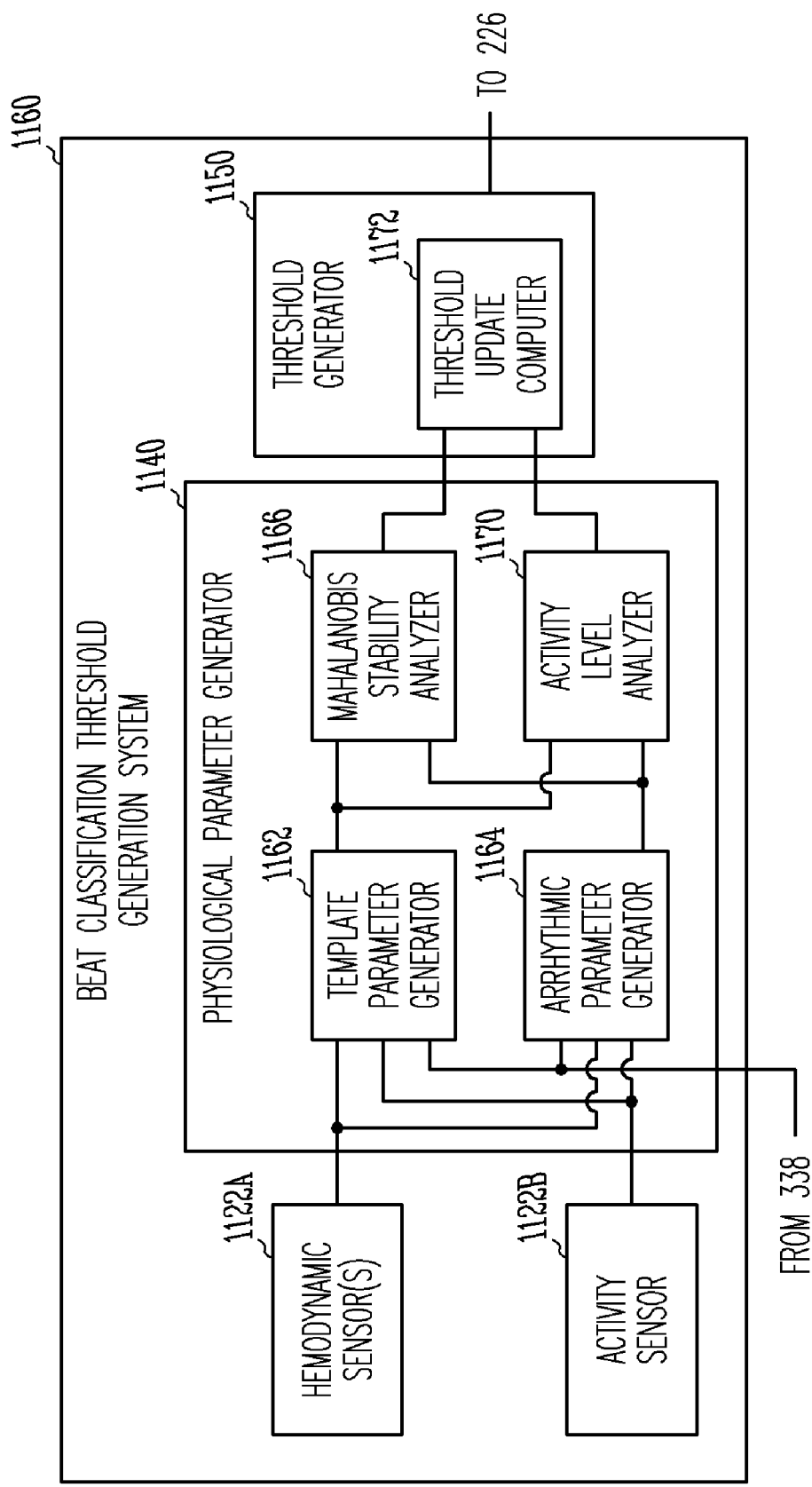
FIG. 11 is a block diagram illustrating another specific embodiment of the beat classification threshold generation system.

FIG. 11 is a block diagram illustrating another specific embodiment of a beat classification threshold generation system 1160, which is a specific embodiment of beat classification threshold generation system 660. Beat classification threshold generation system 1160 includes hemodynamic sensor(s) 1122A, an activity sensor 1122B, a physiological parameter generator 1140, and a threshold generator 1150.

Hemodynamic sensor(s) 1122A and activity sensor 1122B are a specific embodiment of physiological sensor(s) 222. Hemodynamic sensor(s) 1122A includes one or more hemodynamic sensors each sensing a hemodynamic signal indicative of hemodynamic performance. Examples of such hemodynamic sensors include all hemodynamic sensors discussed above in Examples 1 and 2. Examples of activity sensor 1122B include an accelerometer included in ICD 101 or an accelerometer incorporated into a lead of lead system 204.

Physiological parameter generator 1140 is a specific embodiment of physiological parameter generator 340 and derives the hemodynamic stability parameter (S) from the one or more hemodynamic signals sensed by hemodynamic sensor(s) 1122A and the activity parameter (A) from the activity signal sensed by activity sensor 1122B. Physiological parameter generator 1140 includes a template parameter generator 1162, an arrhythmic parameter generator 1164, a hemodynamic stability analyzer 1166, and an activity level analyzer 1170. In one embodiment, the hemodynamic stability parameter (S) is produced using the one or more hemodynamic signals as discussed above in Examples 1 and 2. Template parameter generator 1162 includes template parameter generator 762 to produce the template hemodynamic parameter ($H_T$) or template parameter generator 962 to produce the template parameter vector ($U_T$). Arrhythmic parameter generator 1164 includes arrhythmic parameter generator 764 to measure the arrhythmic hemodynamic parameter ($H_A$) or arrhythmic parameter generator 964 to measure the arrhythmic parameter vector ($U_A$). Hemodynamic stability analyzer 1166 includes hemodynamic stability analyzer 766 to produce the hemodynamic stability parameter (S) using the template hemodynamic parameter ($H_T$) and the arrhythmic hemodynamic parameter ($H_A$) or hemodynamic stability analyzer 966 to produce the hemodynamic stability parameter (S) using the template parameter vector ($U_T$) and the arrhythmic parameter vector ($U_A$). In one embodiment, activity level analyzer 1170 produces the activity parameter (A) being a measure of the activity level by measuring the activity signal sensed by activity sensor 1122B during the detected tachyarrhythmia episode. In another embodiment, template parameter generator 1162 produces a template activity parameter ($A_T$) being a measure of a normal (or expected) activity level such as an activity level during rest or an activity level estimated for a heart rate during hemodynamically tolerable tachyarrhythmia. Arrhythmic parameter generator 1164 measures an arrhythmic activity parameter ($A_A$) being a measure of the activity level during the detected tachyarrhythmia episode. Activity level analyzer 1170 produces the activity parameter (A) as a function of the template activity parameter ($A_T$) and the arrhythmic activity parameter ($A_A$), where the activity parameter (A) is a measure of the deviation of the activity level from the normal level.

Threshold generator 1150 is a specific embodiment of threshold generator 350 and adjusts the beat classification threshold (T) using the hemodynamic stability parameter (S) and the activity parameter (A). In one embodiment, threshold generator 1150 determines the beat classification threshold (T) using the hemodynamic stability parameter (S), as discussed above in Examples 1 and 2, and adjusts the beat classification threshold (T) for the activity parameter (A). For example, when the beat classification threshold (T) corresponds to the minimum value of a correlation coefficient above which an arrhythmic is classified as an SVT beat, threshold generator 1150 decreases the beat classification threshold (T) for a value of the activity parameter (A) that indicates an elevated activity level. This incorporates the effect of exercise, for example, into the morphology-based tachyarrhythmia classification. In one embodiment, threshold generator 1150 includes a threshold update computer 1172. Threshold update computer 1172 monitors any substantial changes in the hemodynamic stability parameter ($\Delta S$) and any substantial change in the activity parameter ($\Delta A$). In response to a change in the hemodynamic stability parameter ($\Delta S$), threshold update computer 1172 computes a change in the beat classification threshold related to hemodynamic stability ($\Delta T_S$).

In response to a change in the activity parameter ($\Delta A$), threshold update computer 1172 computes a change in the beat classification threshold related to activity ($\Delta T_A$). The overall change in the beat classification threshold (T) is then determined by:

$$\Delta T = \alpha \cdot \Delta T_S + \Delta T_A, \quad [6]$$

where $\alpha$ and $\beta$ are empirically determined constants. Threshold generator 1150 updates the beat classification threshold (T) by the change in the beat classification threshold ($\Delta T$). That is, $$T_{new} = T_{old} + \Delta T, \quad [7]$$

where $T_{new}$ is the updated beat classification threshold, and $T_{old}$ is the beat classification threshold before the update.

Figure 12:
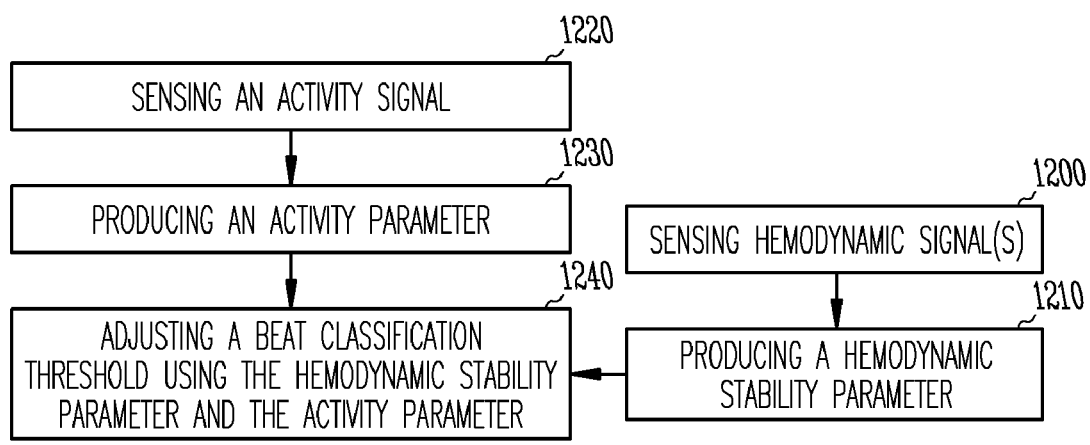
FIG. 12 is a flow chart illustrating another specific embodiment of the method for adjusting the beat classification threshold.

FIG. 12 is a flow chart illustrating another specific embodiment of the method for adjusting the beat classification threshold. In one embodiment, the method is performed by beat classification threshold generation system 1160.

One or more hemodynamic signals each indicative of hemodynamic performance are sensed at 1200. A hemodynamic stability parameter (S) is produced using the one or more hemodynamic signals at 1210, using one of the methods discussed above in Examples 1 and 2. An activity signal indicative of an activity level is sensed at 1220. An activity parameter (A) indicative of the activity level is produced using the activity signal at 1230. In one embodiment, the activity parameter (A) is a measure of the activity level during the detected tachyarrhythmia episode. In another embodiment, the activity parameter (A) is a measure of the deviation of the activity level from its normal level. In this embodiment, a template activity parameter ($A_T$) is produced as a measure of the normal level. An arrhythmic activity parameter ($A_A$) is measured to indicate the activity level during the detected tachyarrhythmia episode. The activity parameter (A) is produced as a function of the template activity parameter ($A_T$) and the arrhythmic activity parameter ($A_A$).

The beat classification threshold (T) is adjusted using the hemodynamic stability parameter (S) and the activity parameter (A) at 1240. In one embodiment, a hemodynamic stability related beat classification threshold ($T_S$) is produced as a function of the hemodynamic stability parameter (S) as discussed above in Examples 1 and 2. An activity related beat classification threshold ($T_A$) is produced as a given function of the activity parameter (A). The beat classification threshold (T) is determined as a function of the hemodynamic stability related beat classification threshold ($T_S$) and the activity related beat classification threshold ($T_A$). Generally, the activity related beat classification threshold ($T_A$) decreases the overall beat classification threshold (T) when the activity parameter (A) indicates an elevated activity level. In a specific embodiment, the function for producing the activity related beat classification threshold ($T_A$) is empirically derived. In one embodiment, a change in the hemodynamic stability related beat classification threshold ($\Delta T_S$) is determined in response to a substantial change in the hemodynamic stability parameter ($\Delta S$). A change in the activity related beat classification threshold ($\Delta T_A$) is determined in response to a substantial change in the activity parameter ($\Delta A$). The change in the beat classification threshold ($\Delta T$) is determined by using Equation [6]. The beat classification threshold (T) is updated by using Equation [7].

Example 4

Beat Classification Threshold Adjustment Using Heart Rate and Activity Signal

In one embodiment, the beat classification threshold (T) is dynamically adjusted using an arrhythmic heart rate detected during the detected tachyarrhythmia episode and an estimated normal heart rate range. The normal heart rate range is estimated using at least an activity signal indicative of a physical activity level or a hemodynamic signal indicative of hemodynamic performance. In one embodiment, the patient's demographical information (such as age) is also used in the estimation of the normal heart range. The hemodynamic performance in turn indicates a metabolic need. If a detected fast heart rate exceeds a tachyarrhythmia detection threshold rate but falls into the estimated normal heart rate range, the fast heart rate is considered as being resulted from elevated physical activity level and/or metabolic demand, as opposed to a tachyarrhythmia of a pathological origin.

Figure 13:
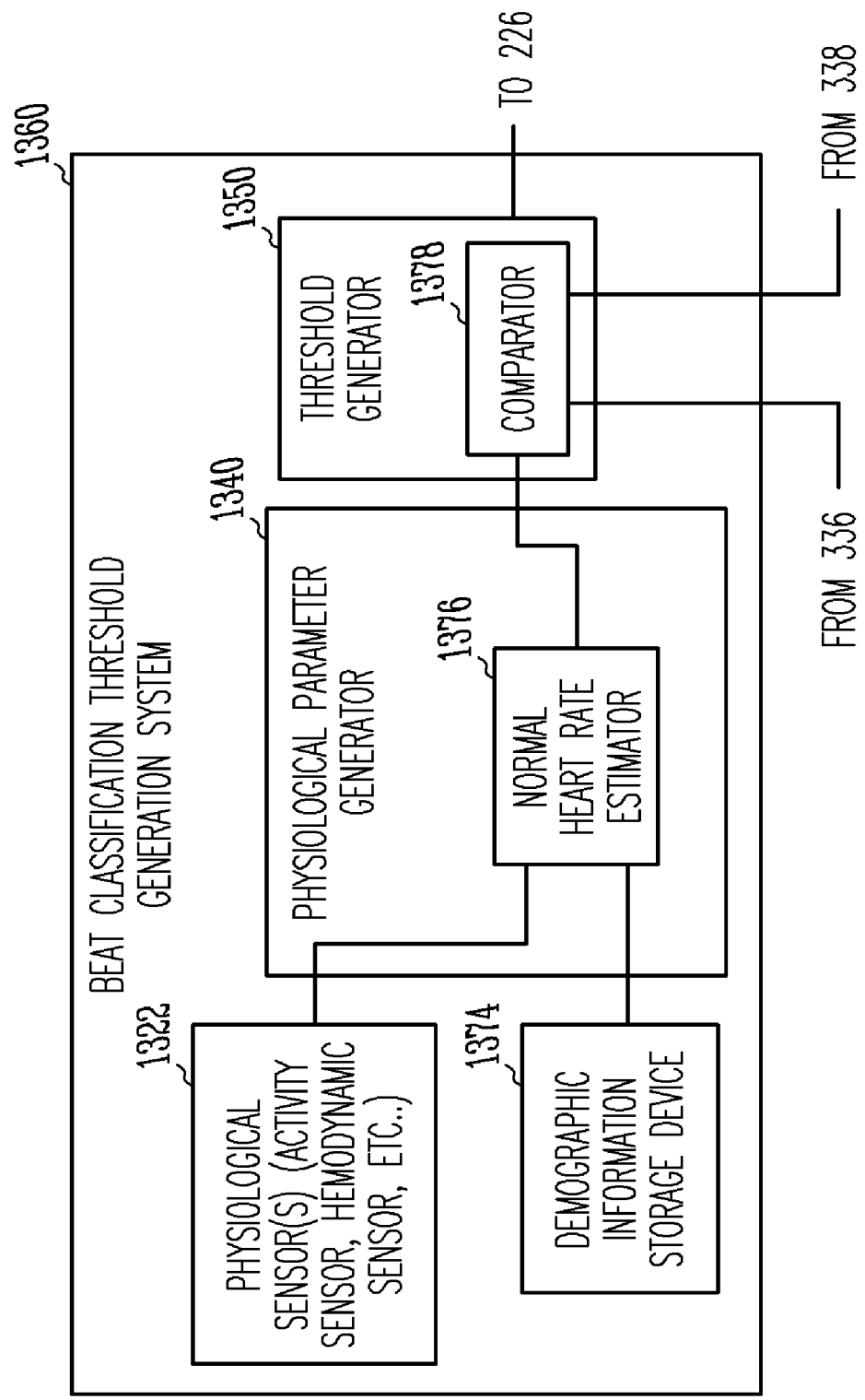
FIG. 13 is a block diagram illustrating another specific embodiment of the beat classification threshold generation system.

FIG. 13 is a block diagram illustrating another specific embodiment of a beat classification threshold generation system 1360, which is a specific embodiment of beat classification threshold generation system 660. Beat classification threshold generation system 1360 includes one or more physiological sensors 1322, a physiological parameter generator 1340, a threshold generator 1350, and a demographic information storage device 1374.

Physiological sensor(s) 1322 is a specific embodiment of physiological sensor(s) 222 and sense one or more physiological signals that provide for an estimation of the normal heart rate range. In one embodiment, physiological sensor 1322 includes an activity sensor to sense an activity signal. Examples of the activity sensor include an accelerometer within ICD 101, an accelerometer incorporated into a lead of lead system 204, and an impedance sensor within ICD 101 that measures transthoracic impedance indicative of respiratory activities (e.g., a minute-ventilation sensor). The normal heart rate range estimated using the activity signal indicates a physiological heart rate range expected for the activity level indicated by the activity signal. In another embodiment, physiological sensor 1322 includes a hemodynamic sensor to sense a hemodynamic signal. The hemodynamic signal has a known approximate relationship with the heart rate. The normal heart rate range estimated using the hemodynamic signal indicates a physiological heart rate range expected for the metabolic demand indicated by the hemodynamic signal.

Physiological parameter generator 1340 is a specific embodiment of physiological parameter generator 340 and includes a normal heart rate estimator 1376. Normal heart rate estimator 1376 estimates normal heart rate range using the one or more physiological signals sensed by physiological sensor(s) 1322, a heart rate detected by rate detector 336 during a known cardiac rhythm such as the NSR, and demographic information of the patient stored in demographic information storage device 1374. The demographic information includes age, gender, and other factors that may physiologically affect the heart rate of the patient.

Threshold generator 1350 adjusts the beat classification threshold (T) using an arrhythmic heart rate detected by rate detector 336 during the detected tachyarrhythmia episode and the estimated normal heart rate range produced by normal heart rate estimator 1376. Threshold generator 1350 includes a comparator 1378 that compares the arrhythmic heart rate to the estimated normal heart rate range. Threshold generator 1350 sets the beat classification threshold (T) to a first predetermined value if the arrhythmic heart rate falls within the estimated normal heart rate range and a second value if the arrhythmic heart rate does not fall within estimated normal heart rate range. In one embodiment, in which the beat classification threshold (T) is used to classify an arrhythmic heart beat as one of VT and SVT, when the arrhythmic heart rate is above the estimated normal heart rate range, the detected tachyarrhythmic episode is more likely a VT episode. Thus, when the known cardiac rhythm is NSR, the second value is set to be substantially higher than the first value.

Figure 14:
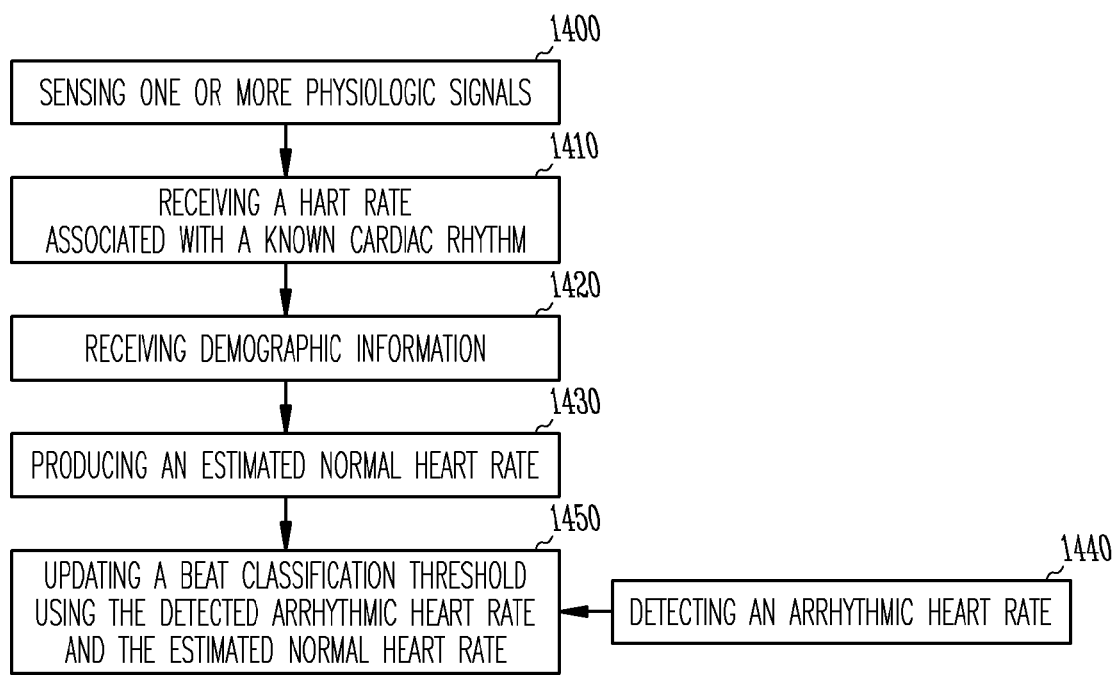
FIG. 14 is a flow chart illustrating another specific embodiment of the method for adjusting the beat classification threshold.

FIG. 14 is a flow chart illustrating another specific embodiment of the method for adjusting the beat classification threshold. In one embodiment, the method is performed by beat classification threshold generation system 1360.

One or more physiological signals are sensed at 1400. Examples of the one or more physiological signals include an activity signal indicative of an activity level and a hemodynamic signal indicative of hemodynamic performance. The hemodynamic signal is of a type that having a known approximate relationship with heart rate. A heart rate associated with a known cardiac rhythm such as the NSR is received at 1410. Demographic information that may affect the heart rate is received at 1420. An estimated normal heart rate range is produced using the one or more physiological signals, the heart rate associated with a known cardiac rhythm, and the demographic information at 1430.

An arrhythmic heart rate is detected during the detected tachyarrhythmia episode at 1440. The beat classification threshold (T) is updated using the arrhythmic heart rate and the estimated normal heart rate range at 1450. In one embodiment, the beat classification threshold (T) is updated by being set to a first predetermined value if the arrhythmic heart rate falls within the estimated normal heart rate range and a second value if the arrhythmic heart rate does not fall within estimated normal heart rate range.

In General

The relationship between a rate and an interval, as used in this document, is the relationship between a frequency and its corresponding period. If a rate is given in beats per minute (bpm), its corresponding interval in millisecond is calculated by dividing 60,000 by the rate (where 60,000 is the number of milliseconds in a minute). Any process, such as a comparison, using the rates is to be modified accordingly when the intervals are used instead. For example, if a tachyarrhythmia is detected when the ventricular rate exceeds a tachyarrhythmia threshold rate, an equivalent process is to detect the tachyarrhythmia when the ventricular interval falls below a tachyarrhythmia threshold interval. The appended claims should be construed to cover such variations. For example, atrial and ventricular intervals should be construed as equivalent to the atrial and ventricular rates, respectively.

It is to be understood that the above detailed description is intended to be illustrative, and not restrictive. For example, tachyarrhythmia detection and classification system 120, including its various embodiments as discussed in this document, is not limited to applications in an ICD, but may be incorporated into any cardiac analysis system, such as a computer program for analyzing pre-collected cardiac data. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A tachyarrhythmia detection and classification system, comprising:
   a cardiac sensing circuit configured to sense at least one cardiac signal;
   a rate detector configured to detect a heart rate from the at least one cardiac signal;
   a tachyarrhythmia detector configured to detect a tachyarrhythmia episode using the heart rate;
   a physiological sensor configured to sense a physiological signal; and
   a morphology-based tachyarrhythmia classification module including:
      a feature extractor configured to extract arrhythmic morphological features of an arrhythmic heart beat of the detected tachyarrhythmia episode from the at least one cardiac signal;
      a similarity analyzer configured to compute a measure of similarity between the arrhythmic morphological features and stored template morphological features of a template heart beat of a known type cardiac rhythm;
      a classifier configured to classify the arrhythmic heart beat as a heart beat of a tachyarrhythmia type having a known morphological relationship with the known type cardiac rhythm in response to the measure of similarity exceeding a dynamically adjustable beat classification threshold (T); and
      a threshold generator configured to adjust the beat classification threshold (T) using an arrhythmic heart rate and an estimated normal heart rate range, the arrhythmic heart rate being the heart rate detected from the at least one cardiac signal during the detected tachyarrhythmia episode, the estimated normal heart rate range being a normal heart rate range estimated using at least the physiological signal.

2. The system of claim 1, wherein the similarity analyzer comprises a correlation analyzer configured to compute a correlation coefficient between the arrhythmic morphological features and the template morphological features for each arrhythmic heart beat of a plurality of arrhythmic heart beats of the detected tachyarrhythmia episode, and the classifier comprises:
- a beat classifier including a beat comparator having a first input to receive the correlation coefficient for each of the plurality of arrhythmic heart beats, a second input to receive the beat classification threshold (T), and an output to indicate a classification for the each of the plurality of arrhythmic heart beats as one of a first type tachyarrhythmic heart beat and a second type tachyarrhythmic heart beat;
- a beat counter configured to count a number of the arrhythmic heart beats classified as the first type tachyarrhythmic heart beat; and
- an episode classifier including an episode comparator having a first input to receive the number of the arrhythmic heart beats classified as the first type tachyarrhythmic heart beat, a second input to receive an episode classification threshold, and an output to indicate a classification of the detected tachyarrhythmia episode as one of a first type tachyarrhythmia and a second type tachyarrhythmia.

3. The system of claim 2, wherein the threshold generator comprises a mapping module to map the physiological signal to values of the beat classification threshold (T).

4. The system of claim 3, wherein the mapping module comprises a look-up table.

5. The system of claim 1, comprising an implantable cardioverter/defibrillator (ICD) including the cardiac sensing circuit, the rate detector, the tachyarrhythmia detector, and the morphology-based tachyarrhythmia classification module.

6. A tachyarrhythmia detection and classification system, comprising:
- a cardiac sensing circuit configured to sense at least one cardiac signal;
- a rate detector configured to detect a heart rate from the at least one cardiac signal;
- a tachyarrhythmia detector configured to detect a tachyarrhythmia episode using the heart rate;
- a physiological sensor configured to sense a physiological signal; and
- a morphology-based tachyarrhythmia classification module including:
  - a feature extractor configured to extract arrhythmic morphological features of an arrhythmic heart beat of the detected tachyarrhythmia episode from the at least one cardiac signal;
  - a similarity analyzer configured to compute a measure of similarity between the arrhythmic morphological features and stored template morphological features of a template heart beat of a known type cardiac rhythm;
  - a classifier configured to classify the arrhythmic heart beat using the measure of similarity and a dynamically adjustable beat classification threshold (T); and
  - a threshold generator configured to adjust the beat classification threshold (T) using an arrhythmic heart rate and an estimated normal heart rate range, the arrhythmic heart rate being the heart rate detected from the at least one cardiac signal during the detected tachyarrhythmia episode, the estimated normal heart rate range being a normal heart rate range estimated using at least the physiological signal, the threshold generator including a normal heart rate estimator configured to produce the estimated normal heart rate range using the physiological signal, a normal heart rate associated with a known type cardiac rhythm, and demographic information.

7. The system of claim 6, wherein the physiological sensor comprises an activity sensor to sense an activity signal, and the normal heart rate estimator is configured to produce the estimated normal heart rate range using the activity signal, the normal heart rate, and the demographic information.

8. The system of claim 6, wherein the physiological sensor comprises an impedance sensor to sense an impedance signal indicative of respiratory activities, and the normal heart rate estimator is configured to produce the estimated normal heart rate range using the impedance signal, the normal heart rate, and the demographic information.

9. The system of claim 6, wherein the physiological sensor comprises a hemodynamic sensor to sense a hemodynamic signal having a known approximate relationship with the heart rate, and the normal heart rate estimator is configured to produce the estimated normal heart rate range using the hemodynamic signal, the normal heart rate, and the demographic information.

10. The system of claim 6, wherein the threshold generator comprises a comparator configured to compare the arrhythmic heart rate to the estimated normal heart rate range, and wherein the threshold generator is configured to set the beat classification threshold (T) to a first value in response to the arrhythmic heart rate falling within the estimated normal heart range and a second value in response to the arrhythmic heart rate falling out of the estimated normal heart range.

11. A method for detecting and classifying tachyarrhythmias, the method comprising:
- sensing at least one cardiac signal;
- detecting a heart rate from the at least one cardiac signal;
- detecting a tachyarrhythmia episode from the heart rate;
- extracting arrhythmic morphological features of an arrhythmic heart beat of the detected tachyarrhythmia episode from the at least one cardiac signal;
- computing a measure of similarity between the arrhythmic morphological features and stored template morphological features of a template heart beat;
- classifying the arrhythmic beat as a heart beat of a tachyarrhythmia type having a known morphological relationship with the known type cardiac rhythm in response to the measure of similarity exceeding a dynamically adjustable beat classification threshold (T);
- sensing a physiological signal; and
- adjusting the beat classification threshold (T) using an arrhythmic heart rate and an estimated normal heart rate range, the arrhythmic heart rate being the heart rate detected from the at least one cardiac signal during the detected tachyarrhythmia episode, the estimated normal heart rate range being a normal heart rate range estimated using at least the physiological signal.

12. The method of claim 11, wherein the measure of similarity comprises a correlation coefficient, and wherein classifying the detected tachyarrhythmia episode comprises:
- comparing the correlation coefficient for each arrhythmic heart beat of a plurality of arrhythmic heart beats to the beat classification threshold (T);
- indicating a classification for the each arrhythmic heart beat as one of a first type tachyarrhythmic heart beat and a second type tachyarrhythmic heart beat;
- counting a number of the arrhythmic heart beats classified as the first type tachyarrhythmic heart beat;

comparing the number of the arrhythmic heart beats classified as the first type tachyarrhythmic heart beat to an episode classification threshold; and indicating a classification of the detected tachyarrhythmia episode as a first type tachyarrhythmia in response to the number of the arrhythmic heart beats classified as the first type tachyarrhythmic heart beat being equal to or greater than the episode classification threshold and as a second type tachyarrhythmic heart beat in response to the number of the arrhythmic heart beats classified as the first type tachyarrhythmic heart beat being below the episode classification threshold.

13. The method of claim 12, wherein classifying the detected tachyarrhythmia episode comprises classifying the detected tachyarrhythmia episode as one of supraventricular tachyarrhythmia (SVT) and ventricular tachyarrhythmia (VT).

14. A method for detecting and classifying tachyarrhythmias, the method comprising:
sensing at least one cardiac signal;
detecting a heart rate from the at least one cardiac signal;
detecting a tachyarrhythmia episode from the heart rate;
extracting arrhythmic morphological features of an arrhythmic heart beat of the detected tachyarrhythmia episode from the at least one cardiac signal;
computing a measure of similarity between the arrhythmic morphological features and stored template morphological features of a template heart beat;
classifying the arrhythmic beat as a heart beat of a tachyarrhythmia type having a known morphological relationship with the known type cardiac rhythm in response to the measure of similarity exceeding a dynamically adjustable beat classification threshold (T);
sensing a physiological signal;
adjusting the beat classification threshold (T) using an arrhythmic heart rate and an estimated normal heart rate range, the arrhythmic heart rate being the heart rate detected from the at least one cardiac signal during the detected tachyarrhythmia episode, the estimated normal heart rate range being a normal heart rate range estimated using at least the physiological signal; and
producing the estimated normal heart rate range using the physiological signal, a normal heart rate associated with a known type cardiac rhythm, and demographic information.

15. The method of claim 14, wherein sensing the physiological signal comprises sensing an activity signal, and producing the estimated normal heart rate range comprises producing the estimated normal heart rate range using the activity signal, the normal heart rate, and the demographic information.

16. The method of claim 14, wherein sensing the physiological signal comprises sensing an impedance signal indicative of respiratory activities, and producing the estimated normal heart rate range comprises producing the estimated normal heart rate range using the impedance signal, the normal heart rate, and the demographic information.

17. The method of claim 14, wherein sensing the physiological signal comprises sensing a hemodynamic signal having a known approximate relationship with the heart rate, and producing the estimated normal heart rate range comprises producing the estimated normal heart rate range using the hemodynamic signal, the normal heart rate, and the demographic information.

18. The method of claim 14, wherein adjusting the beat classification threshold (T) comprises setting the beat classification threshold (T) to a first predetermined value in response to the arrhythmic heart rate falling within the estimated normal heart rate range and a second value in response to the arrhythmic heart rate falling out of the estimated normal heart rate range.

19. The method of claim 18, comprising producing the normal heart rate associated with the known type cardiac rhythm by detecting the heart rate from the at least one cardiac signal during normal sinus rhythm (NSR).

20. A tachyarrhythmia detection and classification system, comprising:
means for sensing at least one cardiac signal;
means for detecting a heart rate from the at least one cardiac signal;
means for detecting a tachyarrhythmia episode from the heart rate;
means for extracting arrhythmic morphological features of an arrhythmic heart beat of the detected tachyarrhythmia episode from the at least one cardiac signal;
means for computing a measure of similarity between the arrhythmic morphological features and stored template morphological features of a template heart beat;
means for classifying the arrhythmic beat as a heart beat of a tachyarrhythmia type having a known morphological relationship with the known type cardiac rhythm in response to the measure of similarity exceeding a dynamically adjustable beat classification threshold (T);
means for sensing a physiological signal; and
means for adjusting the beat classification threshold (T) using an arrhythmic heart rate and an estimated normal heart rate range, the arrhythmic heart rate being the heart rate detected from the at least one cardiac signal during the detected tachyarrhythmia episode, the estimated normal heart rate range being a normal heart rate range estimated using at least the physiological signal.

* * * * *